United States Patent
Backus et al.

(10) Patent No.: US 9,861,477 B2
(45) Date of Patent: Jan. 9, 2018

(54) PROSTHETIC HEART VALVE SQUARE LEAFLET-LEAFLET STITCH

(71) Applicant: BOSTON SCIENTIFIC SCIMED, INC., Maple Grove, MN (US)

(72) Inventors: Andrew J. H. Backus, Santa Cruz, CA (US); John Lin, Milpitas, CA (US); Shannon Elizabeth Kozinn, Los Gatos, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 15/005,081

(22) Filed: Jan. 25, 2016

(65) Prior Publication Data

US 2016/0213467 A1 Jul. 28, 2016

Related U.S. Application Data

(60) Provisional application No. 62/107,605, filed on Jan. 26, 2015.

(51) Int. Cl.
*A61F 2/24* (2006.01)

(52) U.S. Cl.
CPC .......... *A61F 2/2418* (2013.01); *A61F 2/2409* (2013.01); *A61F 2/2415* (2013.01); *A61F 2/2412* (2013.01); *A61F 2220/0008* (2013.01); *A61F 2220/0075* (2013.01); *A61F 2240/001* (2013.01)

(58) Field of Classification Search
CPC ................................ A61F 2/24; A61F 2/2418
USPC ................................................ 623/2.1–2.19
See application file for complete search history.

(56) References Cited

U.S. PATENT DOCUMENTS

| | | |
|---|---|---|
| 15,192 A | 6/1856 | Peale |
| 2,682,057 A | 6/1954 | Lord |
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |

(Continued)

FOREIGN PATENT DOCUMENTS

| | | |
|---|---|---|
| CN | 1338951 A | 3/2002 |
| DE | 19532846 A1 | 3/1997 |

(Continued)

OTHER PUBLICATIONS

US 8,062,356, 11/2011, Salahieh et al. (withdrawn)

(Continued)

*Primary Examiner* — Suzette J Gherbi
(74) *Attorney, Agent, or Firm* — Seager, Tufte & Wickhem LLP

(57) ABSTRACT

A prosthetic heart valve provided herein can include at least two leaflets being secured together along aligned edges thereof by a stitch of a single thread. The stitch includes at least one loop extending through a first aperture, around the aligned edges, and back through the first aperture.

18 Claims, 17 Drawing Sheets

(56) References Cited

U.S. PATENT DOCUMENTS

| | | |
|---|---|---|
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,388,735 A * | 6/1983 | Ionescu ............... A61F 2/2418 623/2.19 |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |

(56) References Cited

U.S. PATENT DOCUMENTS

| | | |
|---|---|---|
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |

(56) References Cited

U.S. PATENT DOCUMENTS

| | | |
|---|---|---|
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 * | 1/2004 | Myers ............... A61F 2/2412 623/2.12 |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |

(56) References Cited

U.S. PATENT DOCUMENTS

| | | |
|---|---|---|
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,778,020 B2 * | 7/2014 | Gregg .................. A61F 2/24 623/2.13 |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0195620 A1 * | 10/2003 | Huynh .................. A61F 2/2409 623/2.14 |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |

(56) References Cited

U.S. PATENT DOCUMENTS

| | | |
|---|---|---|
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0023120 A1* | 1/2010 | Holecek ............... A61F 2/2412 623/2.19 |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |

(56) References Cited

U.S. PATENT DOCUMENTS

| | | |
|---|---|---|
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0116778 A1* | 5/2013 | Gregg ............... A61F 2/24 623/2.13 |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 199007646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0051451 A2 | 5/1982 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| EP | 2614794 A1 | 7/2013 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| TK | 9836790 A1 | 8/1998 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A2 | 9/2004 |
| WO | 2004089250 A1 | 10/2004 |

(56) References Cited

FOREIGN PATENT DOCUMENTS

| | | |
|---|---|---|
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |
| WO | 2013070896 A1 | 5/2013 |
| WO | 2014203106 A1 | 12/2014 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, May, 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al. "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. Feb. 27, 2004.
Stassano. "Mid-term Results of the Valve-on-Valve Technique for Bioprosthetic Failure." European Journal of Cardiothoracic Surgery: vol. 18, 453-457, Oct. 2000.
Topol. "Percutaneous Expandable Prosthetic Valves." Textbook of Interventional Cardiology, W.B. Saunders Company, 2: 1268-1276, 1994.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Cunanan et al., "Tissue Characterization and Calcification Potential of Commercial Bioprosthetic Heart Valves." Ann. Thorac. Surg., S417-421, May 15, 2001.
Examiner's First Report on AU Patent Application No. 2011202667, dated May 17, 2012.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
Levy, "Mycobacterium Chelonei Infection of Porcine Heart Valves." The New England Journal of Medicine, Washington DC, 297(12), Sep. 22, 1977.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
Andersen et al., "Transluminal implantation of artificial heart valves. Description of a new expandable aortic valve and initial

(56) References Cited

OTHER PUBLICATIONS results with implantation by catheter technique in closed chest pigs." Euro. Heart J., 13:704-708, 1992.
Atwood et al., "Insertion of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses." Pergamon Publishing Corporation. New York, 1991: 307-322.
Boudjemline et al. "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcific Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759, 2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Moulopoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Paniagua et al., "Heart Watch." Texas Heart Institute. Spring, 2004. Edition: 8 pages.

Pavcnik et al., "Percutaneous Bioprosthetic Veno Valve: A Long-term Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. 9-17, 2004.
Vahanian et al., "Percutaneous Approaches to Valvular Disease." Circulation, 109: 1572-1579, 2004.
Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
"A Matter of Size." Treiennial Review of the National Nanotechnology Initiative, The National Academies Press, Washington DC, v-13, 2006, http://www.nap.edu/catalog/11752/a-matter-of-size-triennial-review-of-the-national-nanotechnology.
Atwood et al., "Insertion of Heart Valves by Catheterization." The Capstone Design Course Report. MIME 1501-1502. Technical Design Report. Northeastern University, pp. 1-93, Nov. 5, 2007.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report dated Aug. 10, 2011 for EP Application No. 06824992.9.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, 2006.
Supplemental Search Report from EP Patent Office, EP Application No. 05758878.2, dated Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano. "Mid-term Results of the Valve-on-Valve Technique for Bioprosthetic Failure." European Journal of Cardiothoracic Surgery: 453-457, 2000.
International Search Report and Written Opinion PCT/US2016/014878, dated Apr. 21, 2016.
International Preliminary Report on Patentability and Written Opinion dated Aug. 10, 2017 for International Application No. PCT/US2016/014878.

\* cited by examiner

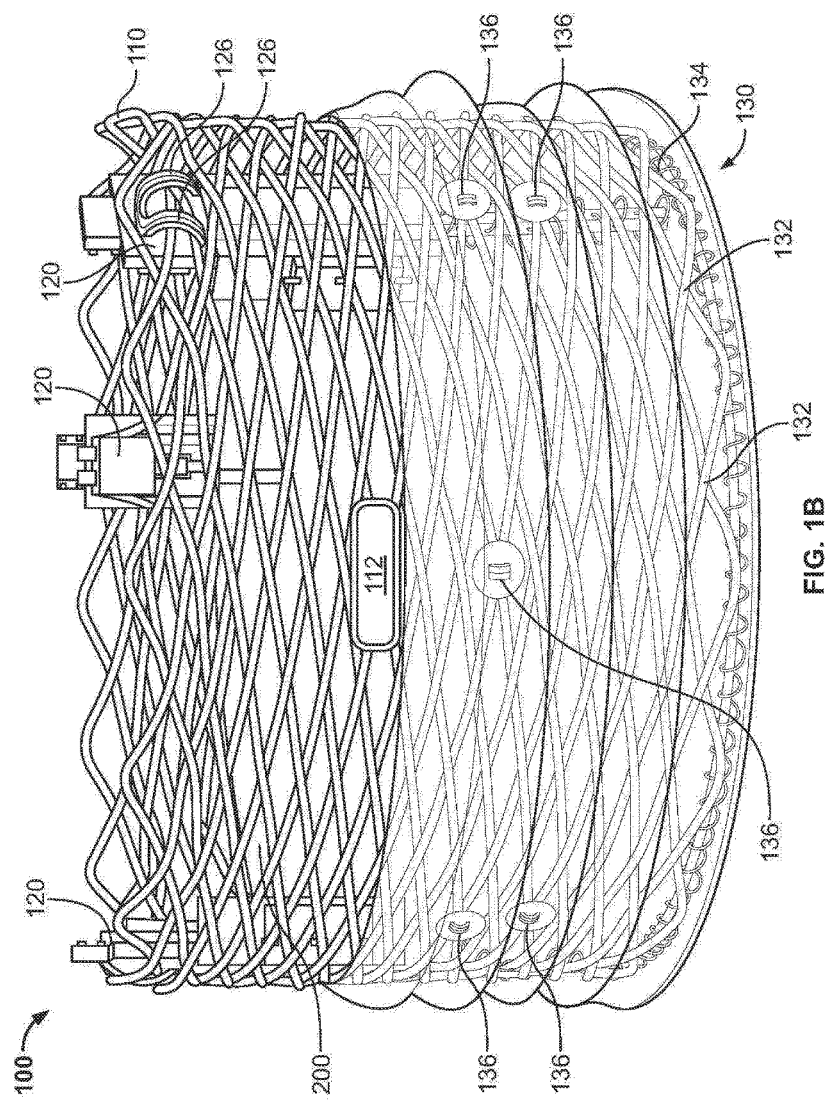

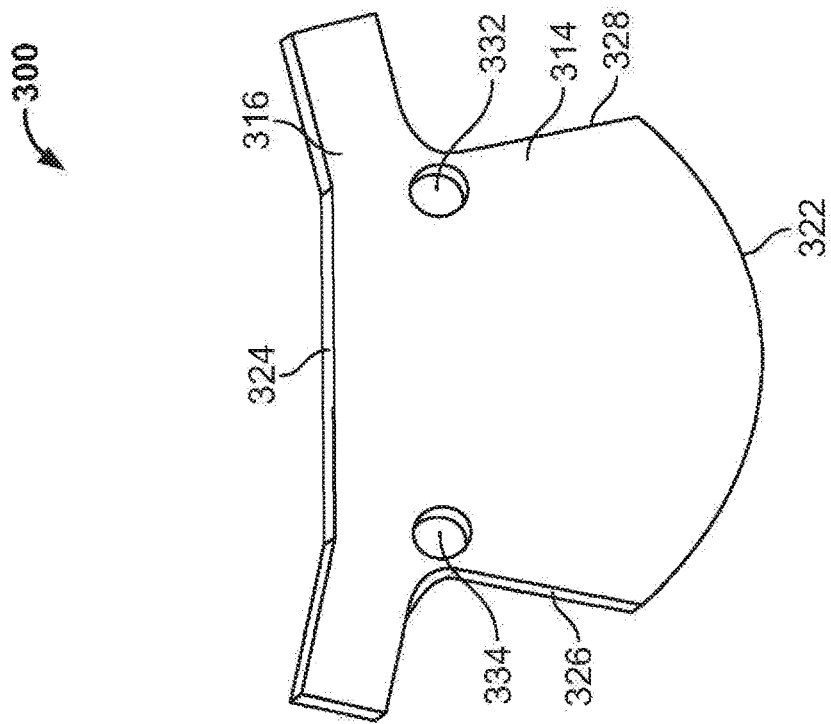
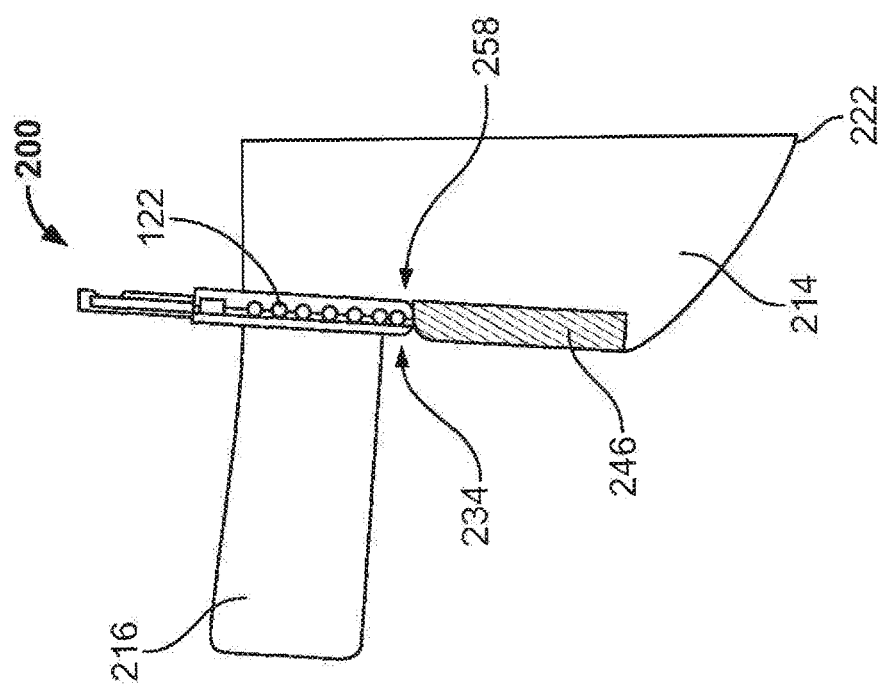

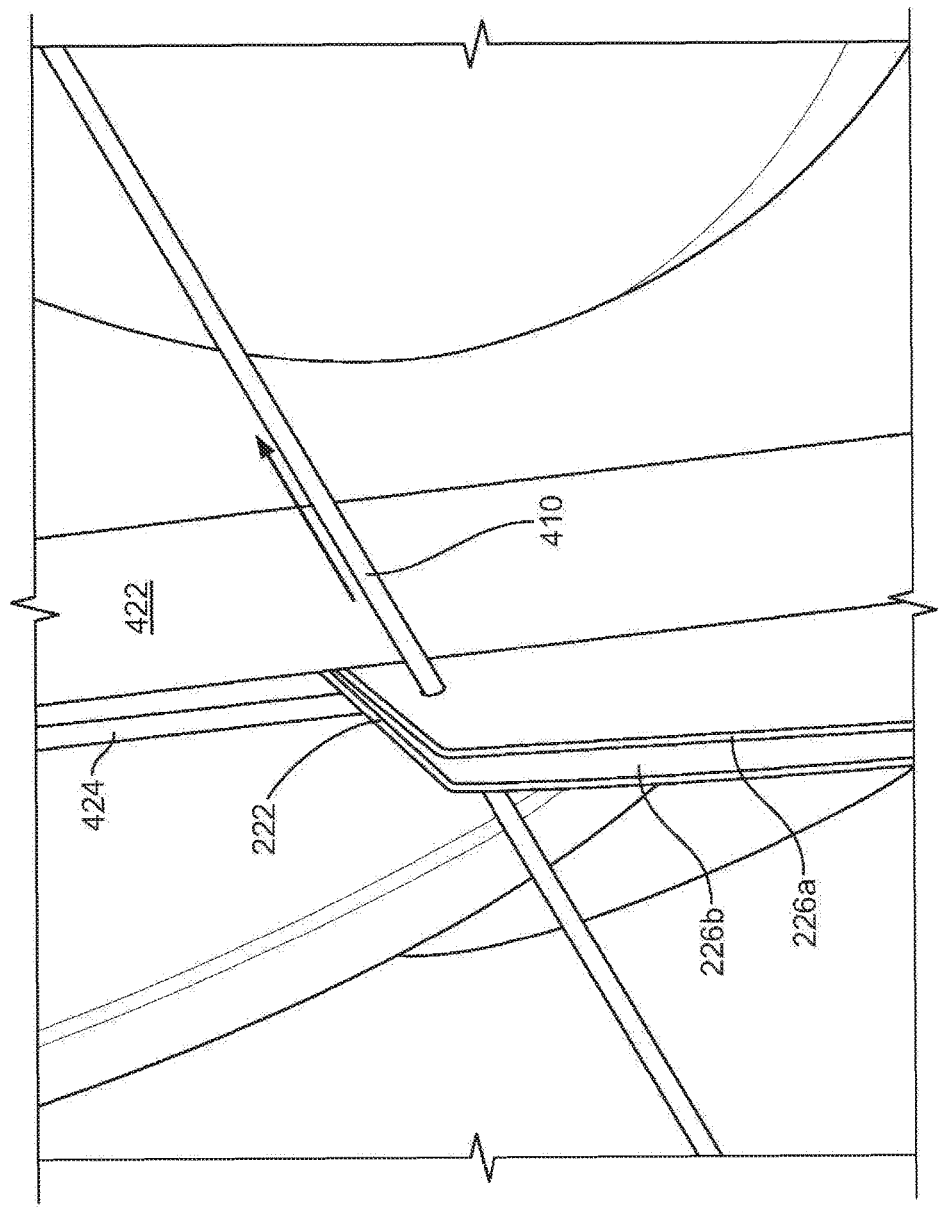

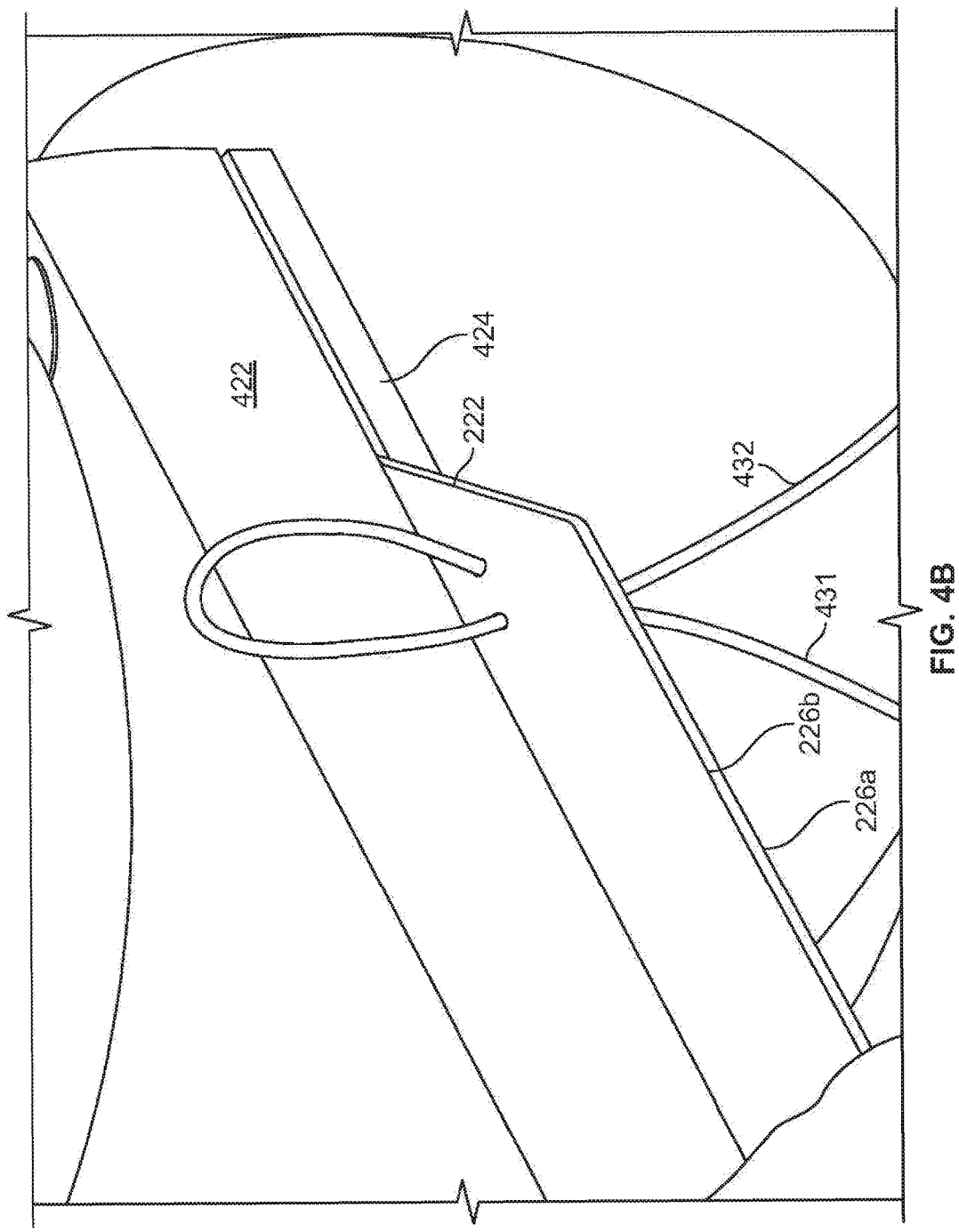

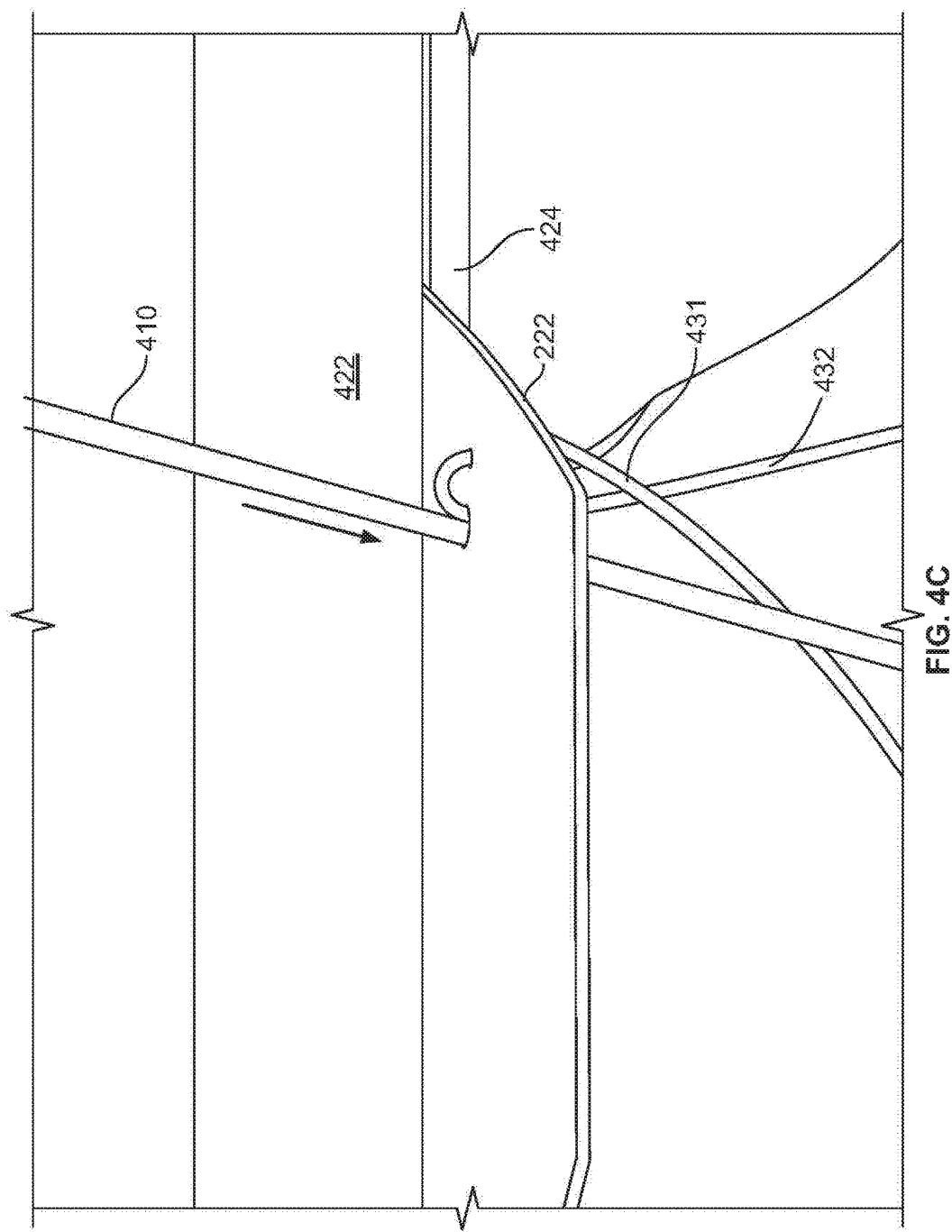

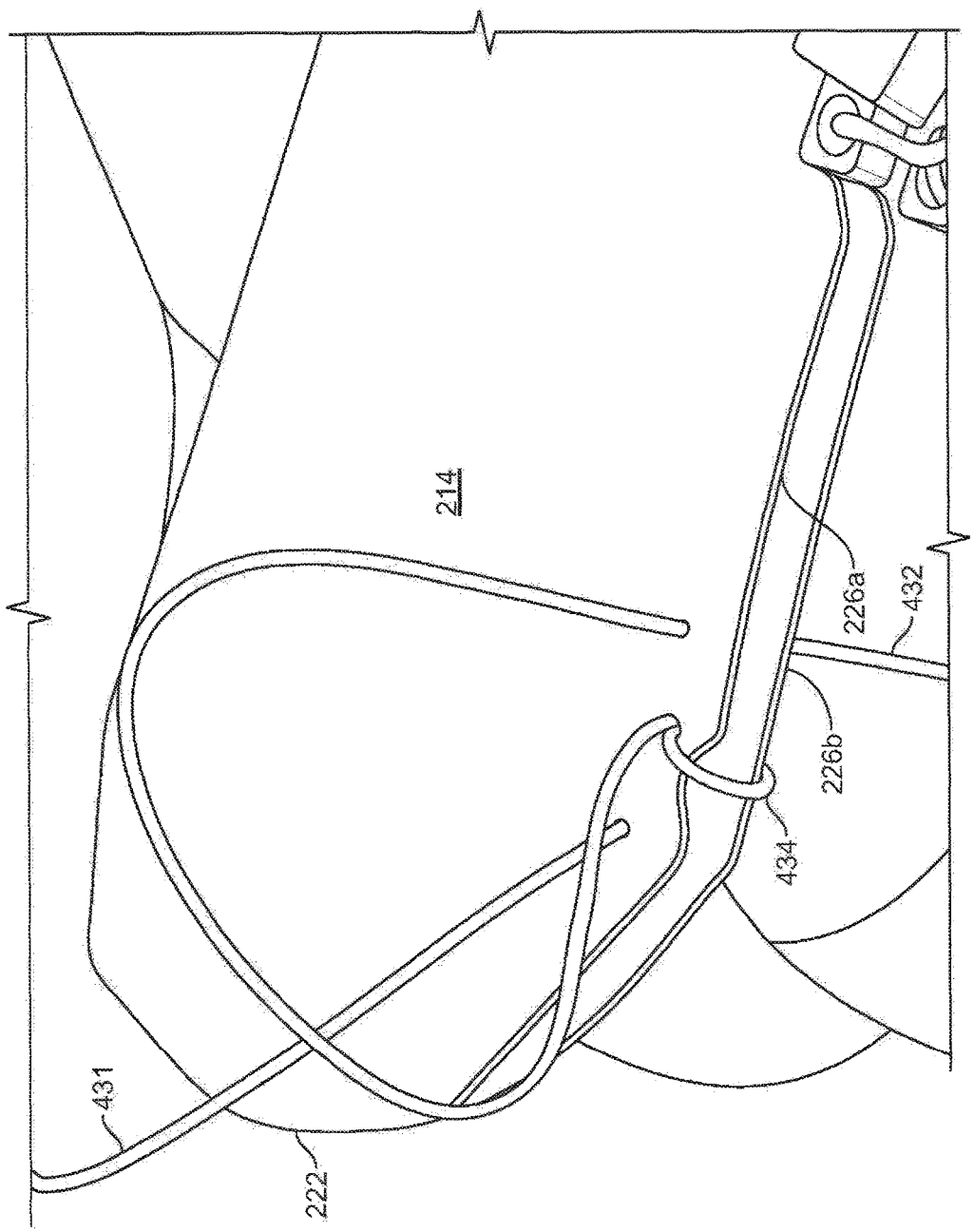

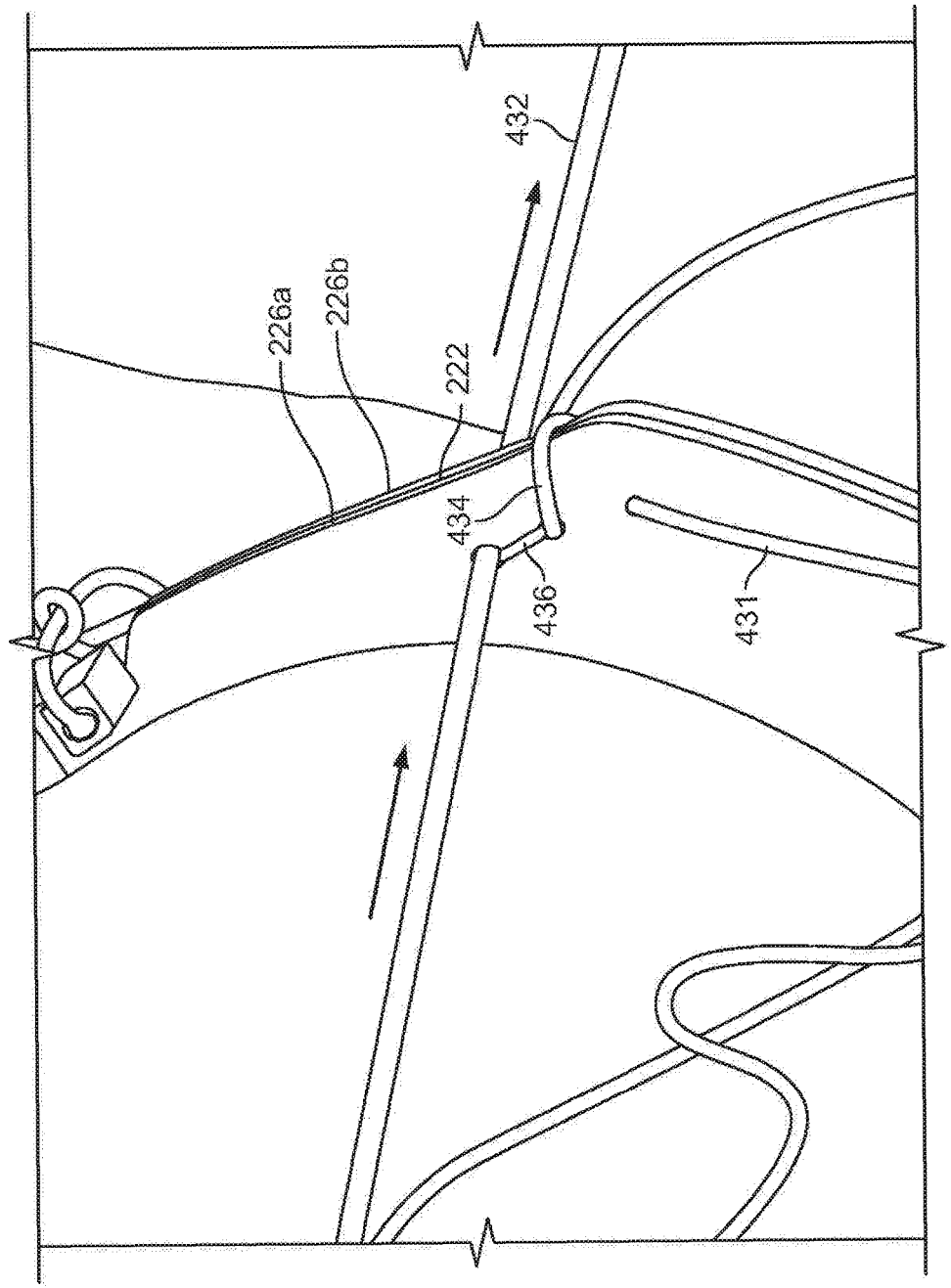

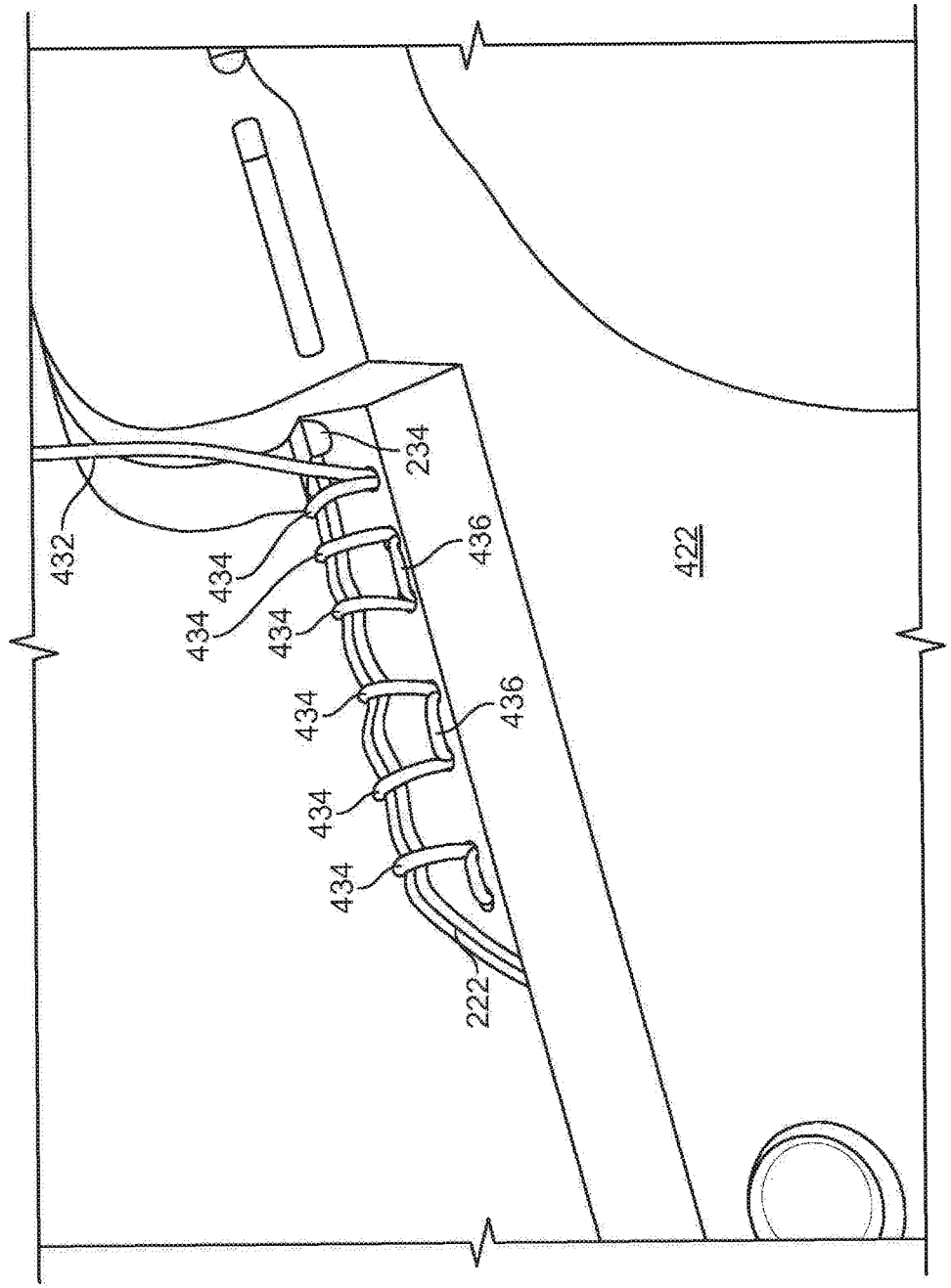

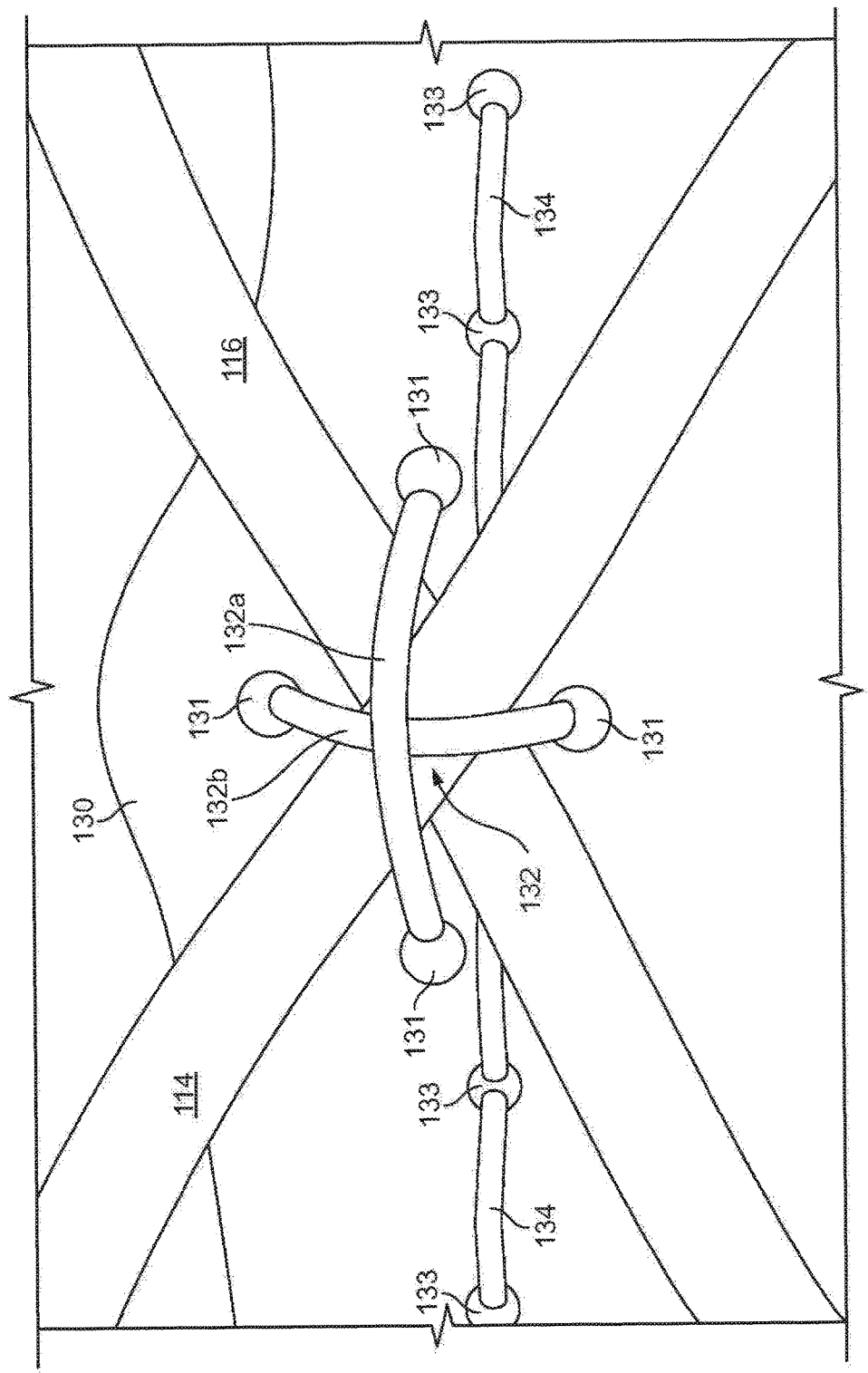

PROSTHETIC HEART VALVE SQUARE LEAFLET-LEAFLET STITCH

RELATED APPLICATIONS

This application claims priority to U.S. Provisional Application Ser. No. 62/107,605, filed Jan. 26, 2015.

FIELD

This document provides prosthetic heart valves having square leaflet-leaflet stitches.

BACKGROUND

The human heart contains four valves: tricuspid valve, pulmonic valve, mitral valve and aortic valve. Their main purpose is to maintain unimpeded forward flow through the heart and from the heart into the major blood vessels connected to the heart, the pulmonary artery and the aorta. As a result of a number of disease processes, both acquired and congenital, any one of the four heart valves may malfunction and result in either stenosis (impeded forward flow) and/or backward flow (regurgitation). Either process burdens the heart and may lead to serious problems including heart failure. Various procedures for fixing or replacing defective heart valves are known in the art. In some cases, artificial heart valves can be implanted in the heart of a patient to replace a diseased or damaged heart valve with a prosthetic equivalent.

Prosthetic heart valves can have a variety of designs. Two major types of prosthetic heart valves include mechanical heart valves and bioprosthetic heart valves. Mechanical heart valves can be made of synthetic materials, such as plastics or metals, while bioprosthetic heart valves can be made of biologic tissue mounted on a fabric covered plastic or metal frame. Bioprosthetic heart valves can include animal tissue, such as porcine or bovine tissue, that has been chemically treated to make the valve suitable for implantation in a human. Bioprosthetic valves do not generally require a patient to undergo anticoagulant therapy, which is typically required when using mechanical valves. As such, there is a need to further improve the design of bioprosthetic valves to retain its functionality during the life of the patient and minimize stenosis and regurgitation.

SUMMARY

Prosthetic heart valves provided herein can have a structure adapted to retain functionality during the life of the patient and to minimize stenosis and regurgitation by having an improved connection between different parts of the prosthetic heart valve. Prosthetic heart valves provided herein can additionally have a reduced unexpanded profile. In some cases, prosthetic heart valves provided herein include a plurality of anchor elements. In some cases, anchor elements can be secured to an expandable tubular member. In some cases, the expandable tubular member can be a braided stent. In some cases, prosthetic heart valves provided herein include three or more leaflets. In some cases, the leaflets can have a body portion and sleeve portions one or both sides. In some cases, sides of the body portions can be secured together and sleeve portions secured to anchor elements (e.g., anchor elements attached to a braided stent). In some cases, anchor elements can include post leg structures adapted to compress and support sleeve portions of leaflets. In some cases, prosthetic heart valves provided herein can include a tubular seal. In some cases, the tubular seal can be secured to bottom edges of body portions of the leaflets. In some cases, the seal can be secured to a blood inlet side of an expandable member.

In some aspects, prosthetic heart valves provided herein include a square stitch between leaflets.

In some aspects, a prosthetic heart valve can include at least two leaflets that are secured together along aligned edges thereof by a stitch of a single thread. The stitch can have at least one loop extending through a first aperture, around the aligned edges, and back through the first aperture.

In some cases, the stitch can have at least one segment of thread extending from the first aperture to a second aperture in a direction parallel to the aligned edges of the at least two leaflets. In some cases, the stitch can have a second loop extended through the second aperture, around the aligned edges, and back through the second aperture. In some cases, the stitch can have at least three loops each extending from an aperture, around the aligned edges, and back to that aperture. In some cases, the stitch runs in a forward direction having thread pass through a set of apertures and back in a reverse direction having the thread again pass through the set of apertures. In some cases, each aperture has two loops extending from that aperture, around the aligned edges, and tack to that aperture, wherein one loop is from the stitch running in the forward direction and one loop is from the stitch running in the reverse direction. In some cases, segments of thread extending between adjacent apertures in the forward direction are on an opposite side of the two leaflets from the segments of thread extending between adjacent apertures in the reverse direction.

In some cases, each leaflet has a body portion and two opposite sleeve portions, the body portion being defined by a bottom edge and two side edges adjacent each sleeve portion, wherein each of the at least two leaflets are aligned and stitched along a first side edge. In some cases, the leaflets define notches between the two side edges and the adjacent sleeve portion. In some cases, the stitch runs along a side edge from a bottom edge to a notch. In some cases, the prosthetic heart valve further includes a plurality of support element each supporting sleeve portions each leaflet along a line approximately aligned the stitch.

In some aspects, a prosthetic heart valve includes at least three leaflets, a tubular expandable member and a tubular seal. The at least three leaflets can be secured together along side edges thereof by a stitch. The tubular expandable member can be secured to an out flow end of the at least three leaflets. The tubular seal can be secured to an inflow end bottom edge of the at least three leaflets and to an outer surface of the tubular expandable member.

In some cases, the tubular expandable member is a braided stent. In some cases, the tubular seal is secured to the braided stent by a plurality of cross stitches connecting the tubular seal to a pair of overlapping wire members of the braided stent. In some cases, the tubular seal includes a woven fabric. In some cases, the woven fabric can have a thickness range from about 0.002 inches to about 0.003 inches (about 40 microns to about 80 microns. In some cases, the tubular seal includes a woven fabric within a polymer matrix. In some cases, the at least three leaflets are secured to the tubular seal in a portion of the tubular seal comprising the woven fabric. In some cases, the at least one leaflet includes bovine or porcine pericardium tissue or a synthetic material. In some cases, the stitch is formed using between 3 and 20 apertures and includes between 3 and 40 loops each extending from an aperture, around the aligned side edges, and back to that aperture.

In some aspects, a prosthetic heart valve includes at least three leaflets, a tubular expandable member and a tubular seal. The at least three leaflets can be secured together along side edges thereof by a stitch. At least one leaflet can be secured to at least a second leaflet by a running stitch. The running stitch can be a square stitch. The tubular expandable member can be secured to an out flow end of the at least three leaflets. The tubular seal can be secured to an inflow end bottom edge of the at least three leaflets and to an outer surface of the tubular expandable member.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1H illustrate an exemplary prosthetic heart valve and an exemplary delivery system provided herein. FIG. 1A is a perspective view of the heart valve connected to a deployment device. FIG. 1B is a side view of the exemplary prosthetic heart valve. FIGS. 1C-1H illustrate how the exemplary heart valve provided herein can be delivered by the delivery system.

FIGS. 2A-2C illustrates an exemplary leaflet, which can be used in prosthetic heart valves provided herein. FIG. 2A illustrates a rounded notch in a leaflet where a leaflet can be secured to an adjacent leaflet. FIGS. 2B and 2C illustrate a portion of an exemplary leaflet for prosthetic heart valves. FIG. 2B depicts a rounded notch in an armpit of a leaflet. FIG. 2C depicts attachment elements in the armpit of the leaflet.

FIG. 3 illustrates another exemplary leaflet, which can be used in prosthetic heart valves provided herein.

FIGS. 4A-4G illustrate how adjacent leaflets can be stitched together in prosthetic heart valves provided herein.

FIGS. 5A-5C illustrate a cross stich provided herein for connecting a seal to a braided stent in an exemplary prosthetic heart valve provided herein. FIG. 5A shows a front view of showing apertures in a seal for securing the seal to the braided stent, apertures in a seal for securing the seal to bottom edges of one or more leaflets, circumferential stitch connecting the seal to bottom edges of one or more leaflets, and a stitch connecting the seal to the braided stent. FIG. 5B depicts a close up view of the cross stitch and a portion of the circumferential stitch. FIG. 5C depicts a cross-sectional view showing the cross stitch and a portion of the circumferential stitch.

Like reference symbols in the various drawings indicate like elements.

DETAILED DESCRIPTION

Prosthetic heart valves provided herein can include an improved stitch pattern between adjacent leaflets. In some cases, aligned edges of adjacent leaflets can be connected by a stitch of a single continuous thread including at least one loop extending through a first aperture, around the aligned edges, and back through the first aperture. As the term is used herein, this loop from an aperture around the aligned edges, and back through the same aperture stitch can be considered a "square stitch." The single continuous thread stitch can additionally include a thread segments that extend from a first aperture to a second aperture in a stitch line extending generally parallel to the aligned edges. In some cases, each aperture in a stitch line can include at least one square stitch. In some cases, the continuous thread stitch can extend in a forward direction and a reverse direction through the same apertures. In some cases, square stitches are formed in each aperture in the forward direction and in the reverse direction such that each aperture includes at least two square stitches. In some cases, segments extending along a surface of a leaflet along the stitch line between adjacent apertures can be formed on opposite sides of the two leaflets in the forward and reverse direction, which can provide a continuous line of compression along the stitch line. The stitch pattern provided herein can provide a secure seal between adjacent leaflets while minimizing the number of apertures, the width of the sealed section, and with a single continuous thread.

Figure 1A:
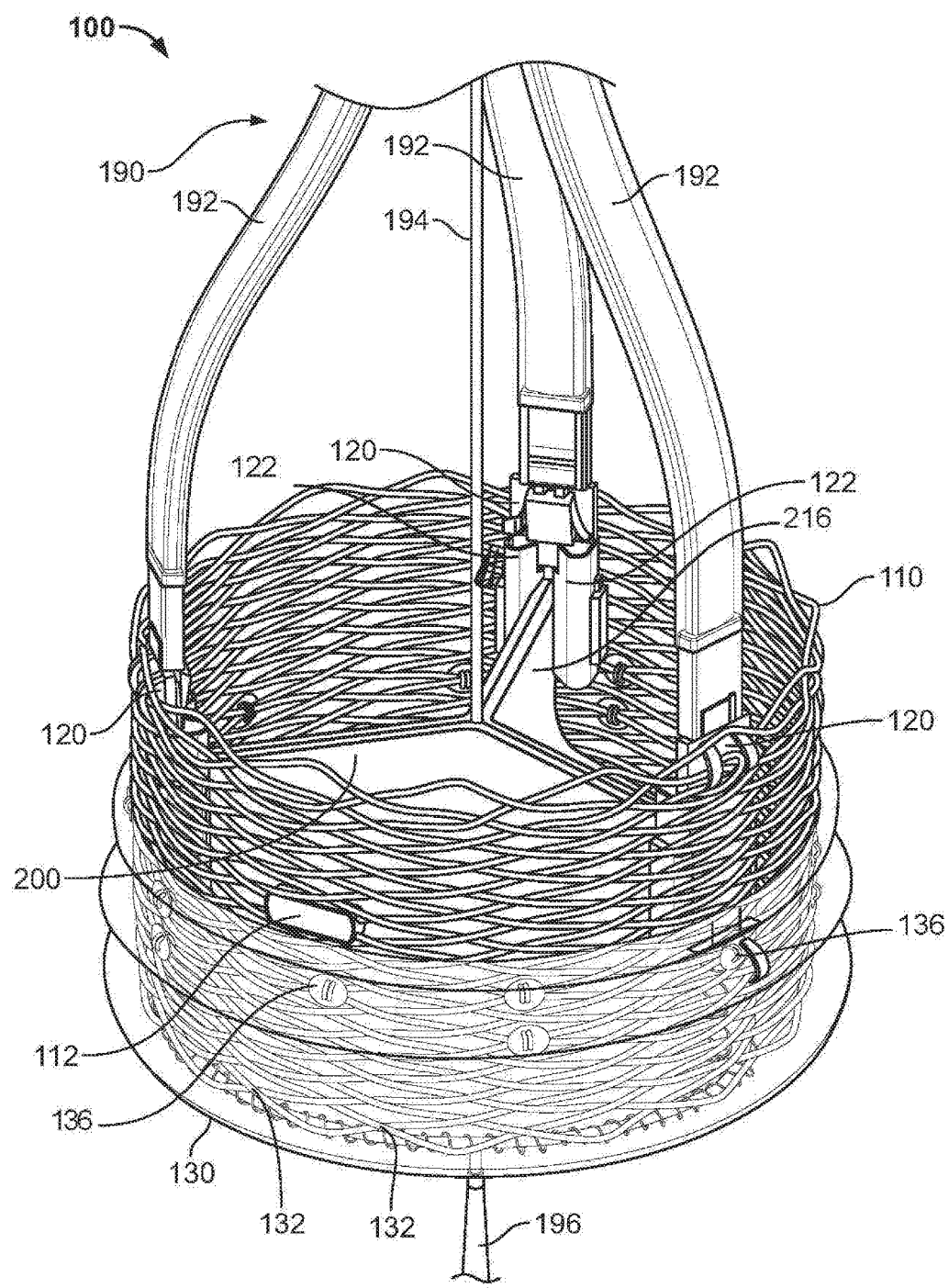
Figure 1C:
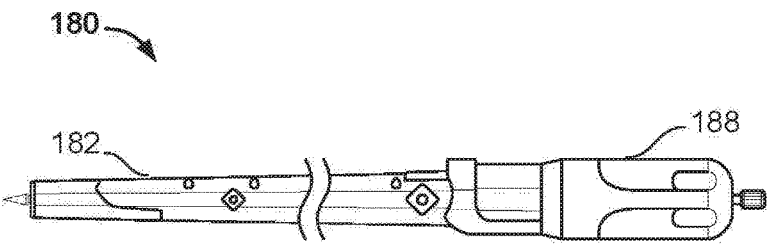
Figure 1D:
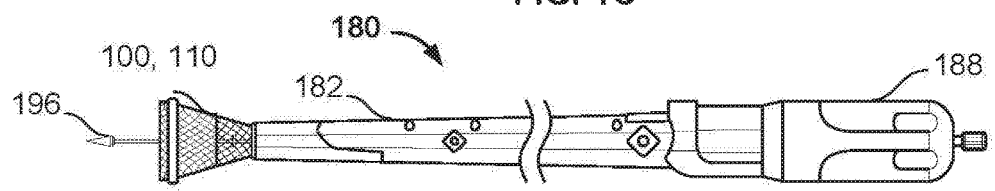
Figure 1E:
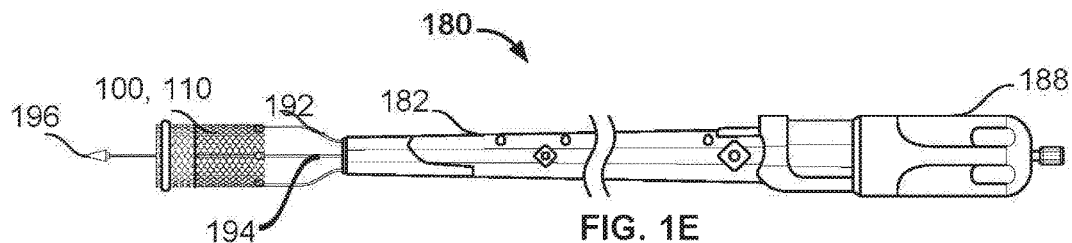
Figure 1F:
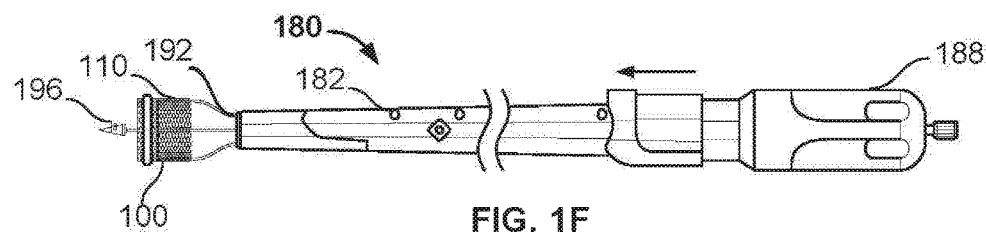
Figure 1G:
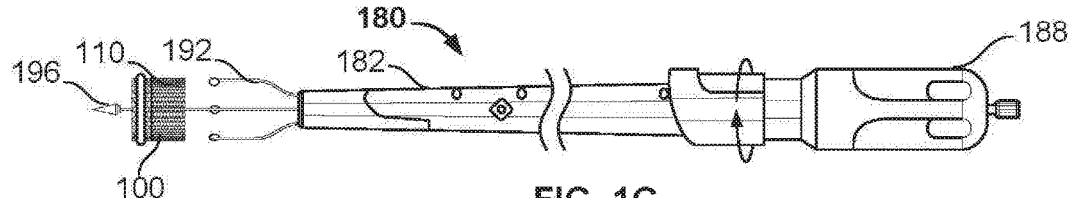
Figure 1H:
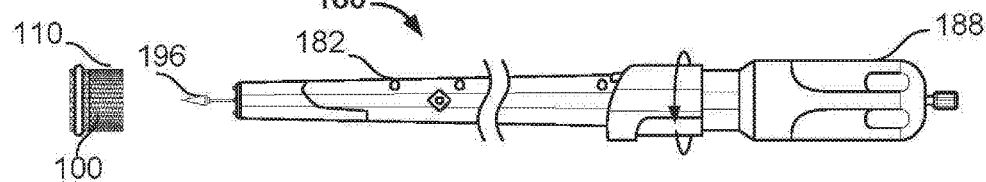

FIGS. 1A and 1B illustrate an exemplary prosthetic heart valve 100 provided herein. FIGS. 1C-1D depict how prosthetic heart valve 100 is deployed. FIG. 1A is a perspective view of prosthetic heart valve 100 connected to a deployment device 190. FIG. 1B is a side view of prosthetic heart valve 100. As shown, prosthetic heart valve 100 includes an expandable member 110, three leaflets 200, three anchor elements 120 securing sleeve portions 216 of leaflets 200 to expandable member 110, a tubular seal 130 secured around a blood inflow end of prosthetic heart valve 100. Anchor elements 120 can include post leg compression elements 122 and clamping support structures 126 adapted to provide support along opposite sides of sleeve portions 216. Expandable member 110 in FIGS. 1A-1D is a braided stent, which is adapted to transition between a restricted state having a smaller diameter and an expanded state having a larger diameter. Expandable member 110 can be self-expanding, mechanically expanded, or a combination thereof.

FIGS. 1C-1H depict an example of how an exemplary heart valve delivery system can deliver the prosthetic heart valve provided herein. As shown in FIGS. 1C-1H, prosthetic heart valve 100 can be deployed using a heart valve delivery system 180. System 180 can include a sheath 182 for retaining the prosthetic heart valve 100 with the expandable member 110 in a restricted state. Within sheath 182, anchor elements 120 (FIGS. 1A and 1B) can be connected to pushing prongs 192 and a pull line 194 can be connected to a nose cap 196, or end cap, positioned at the end of the sheath. As shown in FIG. 1A, the pull line 194 can extend through the expandable member 110 and through the valve opening between leaflets 200. As shown by FIGS. 1D-1H, once a distal end of sheath 182 is delivered through the circulatory system to an appropriate location (e.g., within the heart), prosthetic heart valve 100 can be deployed by advancing pushing prongs 192 and pull line 194 relative to sheath 182 to push prosthetic heart valve 100 out of the sheath 182. In some cases, expandable member 110 can self-expand upon exiting sheath 182. In some cases, expandable member 110 can self-expand to a first intermediate diameter, and system 180 can mechanically expand expandable member 110 to a larger deployment diameter. For example, anchor elements 120 can include a locking mechanism to clip a portion of expandable member when the expandable member 110 is expanded to a predetermined locking diameter. In some cases, system 180 can mechanically expand expandable member 110 to a predetermined locking diameter compressing expandable member 110 between pushing prongs 192 and nose cap 196 by moving pull line 194 relative to pushing prongs 192. The predetermined locking diameter can be a diameter adapted for setting of prosthetic heart valve 100 into surrounding tissue. After prosthetic heart valve 100 is set, system 180 can move pull line 194 and nose cap 196 relative to pushing prongs 192 to move the end cap through the opening between leaflets 200 in prosthetic heart valve 100. Pushing prongs 192 can then be retracted from anchor elements 120 and retracted into sheath 182. In some cases, pushing prongs 192 can include a shape member material adapted to help radially expand expandable member 110 as the expandable member 110 exits sheath 182. A control handle 188 can be used to control the relative movements of sheath 182, pushing prongs 192, and pull wire 194. Prosthetic heart valves provided herein can be adapted to limit damage to the valves during the setting of the valve.

In some cases, one or more radiopaque markers can be secured to prosthetic heart valves provided herein. For example, as shown in FIGS. 1A and 1B, expandable member 110 including a radiopaque marker 112. Any suitable radiopaque material (such a platinum, palladium, gold, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least 3 radiopaque markers.

As shown in FIG. 1A, prosthetic heart valve 100 can include a plurality of leaflets 200. In some cases, such as that shown, prosthetic heart valve 100 includes three leaflets 200. In some cases, prosthetic heart valves provided herein can have any suitable number of leaflets, for example two, three, four, five, or more leaflets. In some cases, leaflets 200 are secured to one another. In some cases, leaflets 200 can be secured to one another via a plurality of sutures. Leaflets 200 can be sutured along side edges of a body portion of each leaflet. In some cases, prosthetic heart valves provide herein can include a single line of sutures, which can be adapted to minimize leaks, minimize an amount of a width of the seam, and/or minimize the profile of the replacement heart valve during percutaneous insertion. In some cases, prosthetic heart valves provide herein can include a multiple lines of sutures.

Expandable member 110 can have any suitable structure, arrangement, or material. In some cases, expandable member 110 can include a braided wire stent. For example, US Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

Figure 2B:
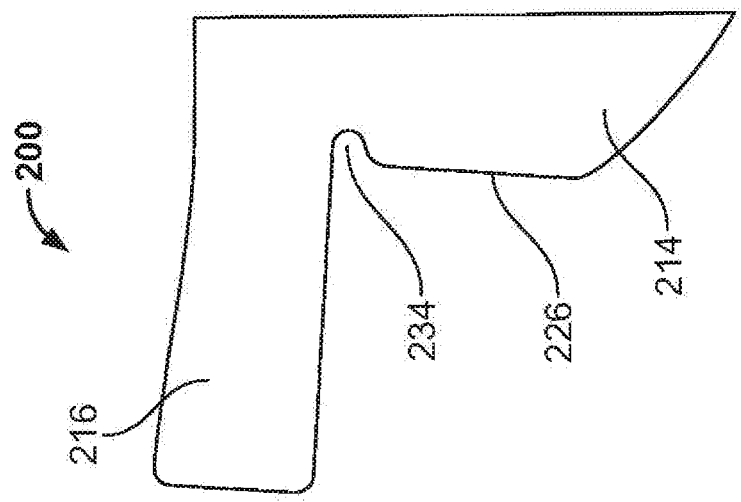
Figure 2A:
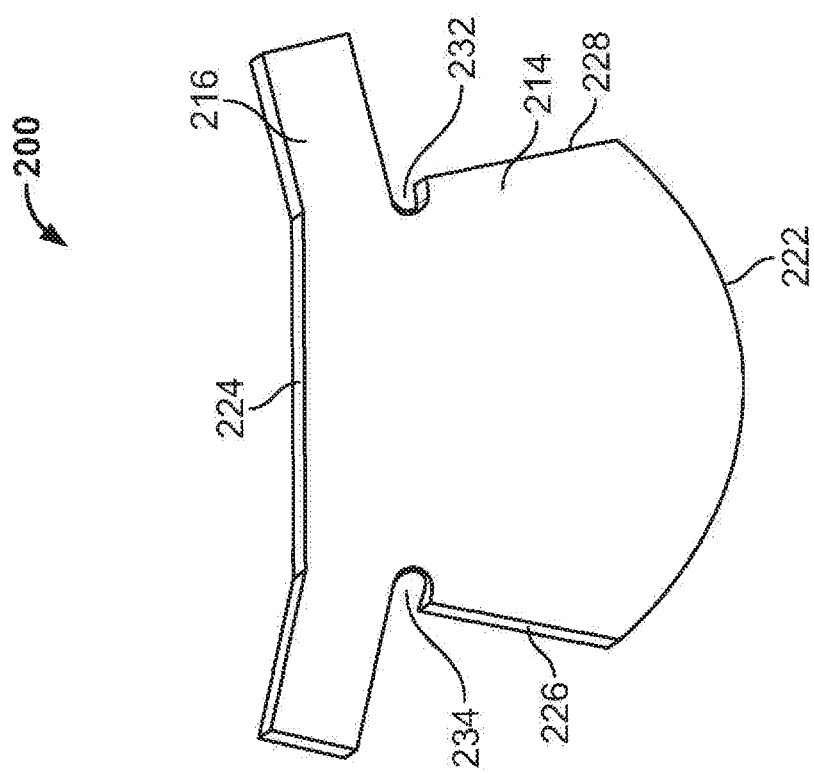

Referring to FIGS. 2A-2C, a leaflet 200 can include a body portion 214 and sleeve portions 216. In some cases, the body portion 214 has a bottom edge 222, a first side edge 226, a second side edge 228, and a free edge 224. Leaflet 200 further includes a front, a back, a first side adjacent to the first side edge 226, and a second side adjacent to the second side edge 228. In some cases, the front of the leaflet 200 has a different texture than the back. In some cases, this occurs where the leaflet 200 is made from pig, cow, or other natural animal tissue. In some cases, leaflet 200 is made from bovine pericardium. Leaflets 200 can also be made from a synthetic material. Leaflets 200 can be assembled by aligning two leaflets 200 to position side regions of opposite leaflets 200 adjacent to each other to stitch the leaflets 200 together along stitch line 246, as shown in FIG. 2C.

As shown in FIGS. 2A-2C, leaflet 200 can define notches 232 and 234 along the side edges 228 and 226 adjacent to sleeve portions 216. Notches 232 and 234 can allow for post leg compression elements 122, which can be a part of anchor elements 120 (shown in FIGS. 1A and 1B), to compress and restrain sleeve portions 216 along the same line as the stitch line 246 without having a suture 258 (FIG. 2C) connecting post leg compression element 122 from abrading leaflets 200 due to the pulsating movement of the leaflets due to the circulatory system. Suture 258 can be used apply an appropriate and consistent compressive force between the post leg compression elements 122 in order to prevent leakage through sleeve portions 216 of the leaflets 200. Positioning the compression line and the stitch line 246 at an offset or at an angle in order to avoid having suture 258 pass through leaflet material can create a stress concentrator, which can result in tears in the leaflet material. Accordingly, a notched leaflet 200 can improve valve opening capabilities and the reliability of prosthetic heart valves provided herein.

FIG. 3 illustrate another exemplary leaflet, which can be used in prosthetic heart valves provided herein. As shown in FIG. 3, leaflet 300 can include a body portion 314 and sleeve portions 316. In some cases, the body portion 314 has a bottom edge 322, a first side edge 326, a second side edge 328, and a free edge 324. Leaflet 300 further includes a front, a back, a first side adjacent to the first side edge 326, and a second side adjacent to the second side edge 328. In some cases, the front of the leaflet 300 has a different texture than the back. In some cases, this occurs where the leaflet 300 is made from pig, cow, or other natural animal tissue. In some cases, leaflet 300 is made from bovine pericardium. Leaflets 300 can also be made from a synthetic material. Leaflets 300 can be assembled by aligning two leaflets 300 to position side regions of opposite leaflets 300 adjacent to each other to stitch the leaflets 300 together along a stitch line positioned in the same way that stitch line 246 is shown in FIG. 2C. Leaflet 300 can define apertures 332 and 334 adjacent the side edges 328 and 326 and adjacent the sleeve portions 316. Apertures 332 and 334 in the leaflets 300 can allow one leaflet to be secured to an adjacent leaflet. Similar to the notches discussed above, apertures 332 and 334 can allow for post leg compression elements, which can be a part of anchor elements 120, to compress and restrain sleeve portions 316 along the same line as a stitch line without having a suture connecting post leg compression element from abrading leaflets 300 due to the pulsating movement of the leaflets due to the circulatory system. Apertures 332 and 334 can have a diameter significantly larger than the diameter of the suture in order to minimize abrasion of the leaflets 300. Accordingly, leaflets 300 used in prosthetic heart valves provided herein can improve the reliability of prosthetic heart valves provided herein.

FIGS. 4A-4G depict an example of how leaflets 200 can be jointed and provide an improved stitch between leaflets. As shown, stitch 446 can be a single continuous line stitch traveling along the stitch line in a forward direction and back in a reverse direction. In some cases, stitch 446 can run along a leaflet from a bottom edge to a side edge of the leaflet, e.g., bottom edge 222 to side edge 226 of leaflet 200 shown in FIG. 2A-2B. In some cases, stitch 446 can run from a side edge to a notch of a leaflet, e.g., side edge 226 to notch 234 of leaflet 200.

As shown in FIGS. 4D-4Q stitch 446 can include a plurality of perpendicular loop segments 434 extending through an aperture in the two leaflets, around outer side edges of the two attached leaflets, and back through the aperture. Stitch 446 can include a plurality of parallel segments 436 extending between adjacent apertures along the stitch line. Stitch 446 can include two perpendicular loop segments 434 extending through apertures formed in the stitch line. In some cases, a first perpendicular loop segment 434 for a first aperture in the stitch line is formed when the stitch is formed in the forward direction and a second perpendicular loop segment 434 for the first aperture is formed in the reverse direction. In some cases, parallel segments 436 made in a forward direction alternate between opposite sides of the two leaflets between each aperture in the stitch line. In some cases, parallel segments 436 made in a reverse direction are formed on an opposite side of the two leaflets from parallel segments 436 made in a forward direction. In some cases, opposite parallel segments 436 made in the forward and reverse directions can provide a continuous compressive force along the entire length of the stitch line. Perpendicular loop segments 434 can provide compressive force to reinforce the seal formed between the two leaflets along the stitch line.

Stitch 446 can include any appropriate number of perpendicular loop segments formed through any appropriate number of apertures. As shown, stitch 446 includes six perpendicular loop segments formed through six apertures (two perpendicular loop segments per aperture). In some cases, stitch 446 can include up to twelve perpendicular loop segments formed through six or more apertures. In some cases, a stitch connecting side edge segments of leaflets can be formed using between 3 and 20 apertures and include between 3 and 40 perpendicular loop segments. In some cases, apertures can be positioned between 0.2 mm and 10 mm apart. In some cases, apertures can be positioned between 0.2 mm and 10 mm away from a side edges of the leaflets.

Figure 4G:
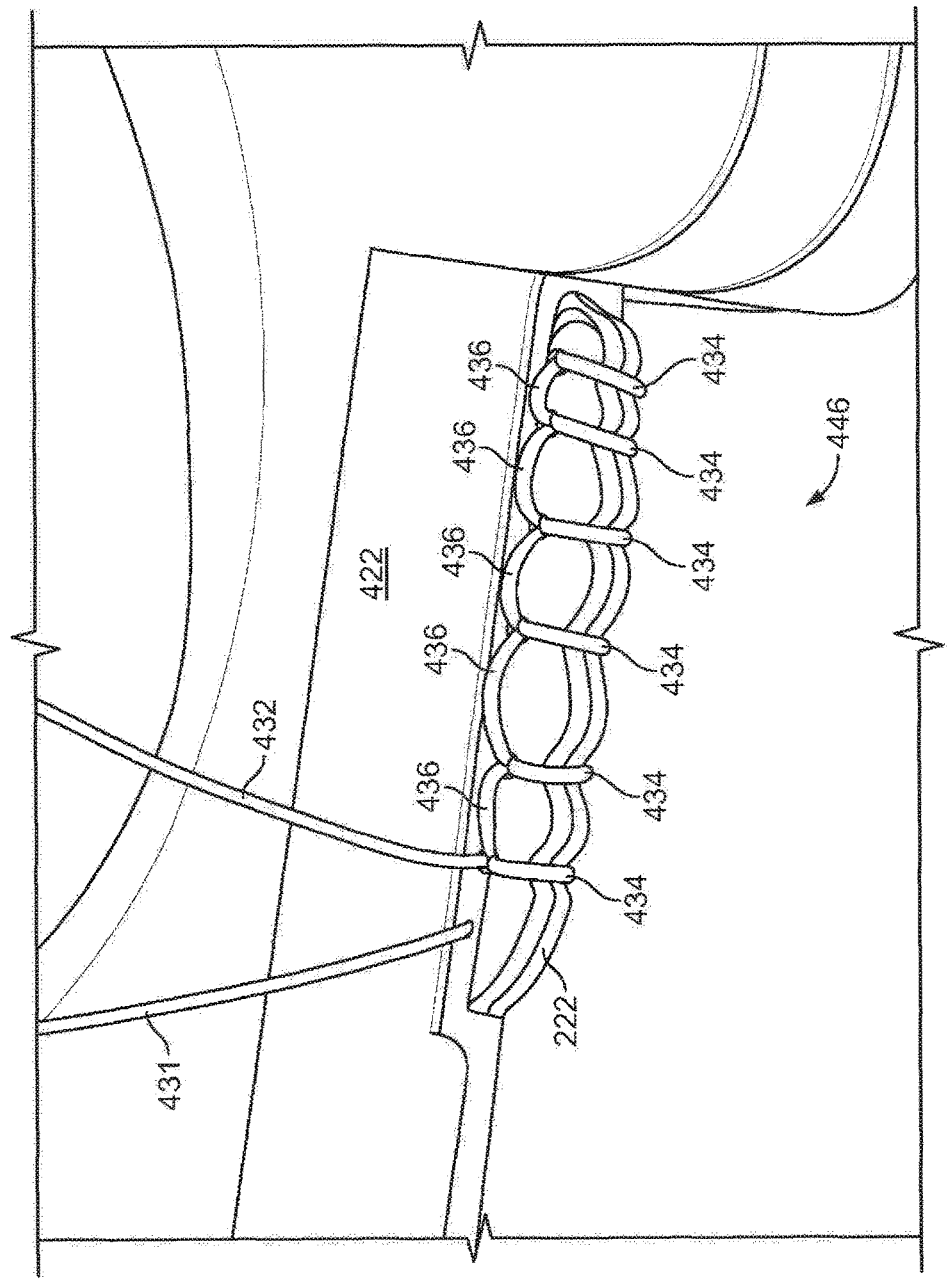

Stitch 446 can be formed in a process depicted in FIGS. 4A-4G As shown in FIG. 4A, a thread needle 410 can be passed through aligned leaflet side edges 226a and 226b to create a first aperture in a location near bottom edges 222 approximately 1 mm from the bottom edges 222. The leaflet side edges 226a and 226b can be retained is a desired configuration by clamping the leaflets between clamp sides 422 and 424. Needle 410 pulls a leading end 431 of a thread 432 through the first aperture. As shown in FIG. 4B, needle 410 can then form a second aperture adjacent to the first aperture along the stitch line (towards the leaflet sleeve portion) about 0.5 mm away from the first aperture to pull leading end 431 of thread 432 through the second aperture to form a first parallel segment. As shown in FIG. 4C, a perpendicular loop segment 434 can be made by guiding needle 410 around the leaflet side edges and re-enter the second aperture from a backside. Thread 432 can be pulled through the second aperture until it sits firmly against the leaflet material (e.g., leaflet pericardium tissue). FIG. 4D shows a second parallel segment, which can be made by pushing needle 410 through leaflet tissue along the stitch line to form a third aperture approximately 1 mm from the second aperture (towards the sleeve segments of the leaflet). As shown in FIG. 4E, a second perpendicular loop segment 434 can be formed by again having needle 410 loop around the leaflet side edges and reenter the third aperture through the backside. This is repeated up to notch 234 to form a total of six parallel segments 436 and six perpendicular loop segments 434 in a forward direction, as shown in FIG. 4F.

The stitch pattern can then be repeated in a reverse direction towards bottom edges 222 of the leaflets through the previously formed apertures to have each aperture include two perpendicular loop segments 434 and create parallel segments on opposite sides from the parallel segments created in the forward direction, as shown in FIG. 4G The method and stitches depicted in FIGS. 4A-4G is also envisioned for leaflets 300.

Stitch 446 and other stitches provided herein can improve the reliability of a seal formed along a stitch line, create fewer apertures through the leaflets, and simplify the stitching operation. Fewer apertures can limit an opportunity for blood to leak through the apertures. The single continuous line of stitch 446 using a single row of apertures can minimize a width of a side edge portion needed to form a continuous seal along the side edges of the leaflets, which can allow for a reduce restricted profile for prosthetic heart valves provided herein. For example, U.S. Pat. No. 8,778,020 describes a variety of ways that leaflets can be sutured together using combinations of whip stitches and running stitches, which require additional apertures and multiple lines. Perpendicular loop segments 434 can provide a function similar to the whip stitches discussed in U.S. Pat. No. 8,778,020 and parallel segments 436 can provide a function similar to the running stitches discussed in U.S. Pat. No. 8,778,020. Although stitch 446 can provide an improved attachment between side edges of leaflets in prosthetic heart valves provided herein, some embodiments of prosthetic heart valves provided herein can use other stitch patterns, such as those described in U.S. Pat. No. 8,778,020, which is hereby incorporated by reference.

Several important characteristics of the thread can include, but are not limited to, a tensile strength, abrasion resistance and creep rupture resistance characteristics that can withstand device delivery and implantation. The thread used for suturing together portions of the heart valve, e.g., sides edges of the leaflets, can composed of biocompatible materials that include polyethylene, such as ultra high molecular weight polyethylene (UHMWPE), polyester (PET), and combinations thereof.

Referring back to FIGS. 1A and 1B, prosthetic heart valve 100 can include a tubular seal 130. Tubular seal 130 can be secured to bottom edges 222 (FIG. 2A) of leaflets 200 by a cross stitch 134 within prosthetic heart valve 100. Tubular seal 130 can be secured to expandable tubular member 110 by fasteners 136 and extend around the outside of expandable tubular member 110 to provide a seal to minimize blood leakage around the leaflets 200 when prosthetic heart valve 100 is implanted. The structure and materials of tubular seal 130 are discussed below in reference to FIGS. 6, 7a, and 7b.

Figure 5A:
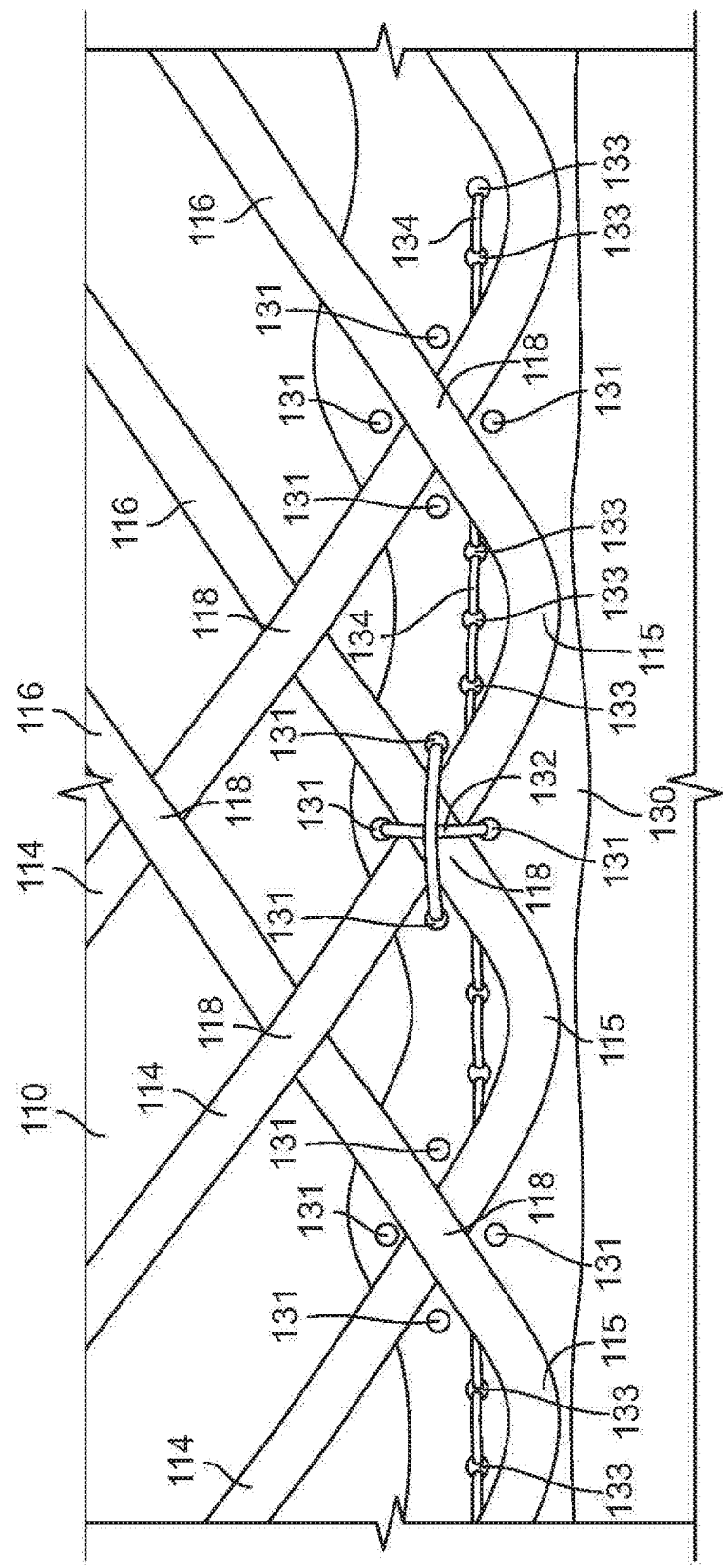
Figure 5C:
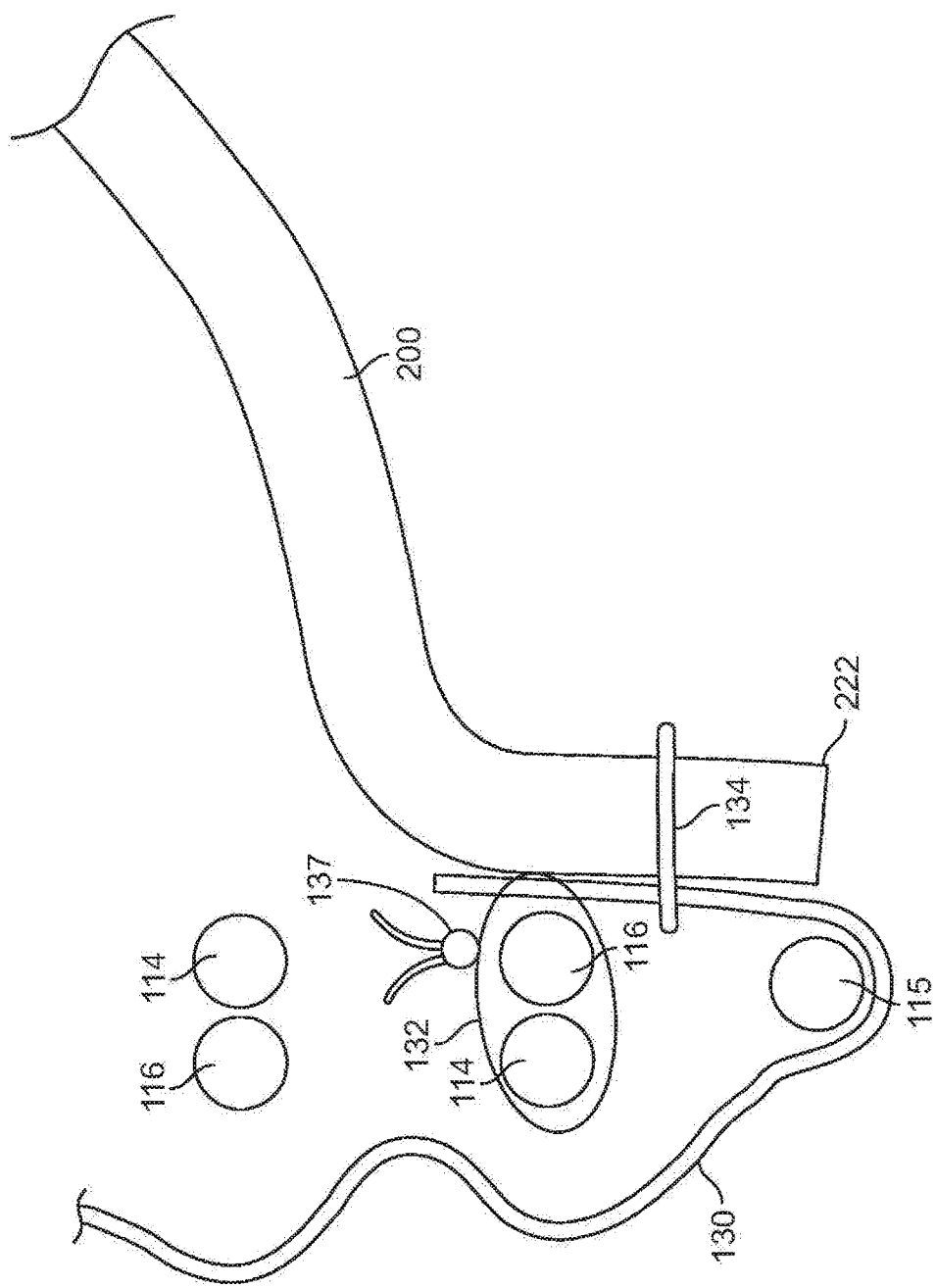

Referring to FIGS. 5A-5C, an improved tubular seal stitching pattern can include a cross stitch 132 between tubular seal 130 and expandable member 110. As shown in FIGS. 1A, 1B, and 5A-5C, expandable member 110 can be a braided stent including one or more wires having a first set of segments 114 extending helically in a first direction and a second set of segments 116 extending helically in a second direction such that the first set of segments 114 cross the second set of segments 116 at intersection points 118. As shown, one or more wires can have inflow crows 115 at an end of the braided stent where the wires transition a first segment 114 to a second segment 116. In some cases, cross stitches 132 secure tubular seal 130 to two crossing segments 114 and 116 of the braided stent at an intersection 118. A separate circumferential running stitch 134 can inserted into preformed apertures 133 to secure the adaptive seal to bottom edges 222 of leaflets 200 shown in FIGS. 2A and 2C.

Cross-stitches around intersections 118 can increase the strength of the attachment of tubular seal 130 to the expandable member 110 while also allowing for improved load transfer to the expandable member 110. In some cases, the cross stitches secure tubular seal 130 at intersections 118 immediately above (proximal) of the inflow crowns 115. Cross stitches 132 can be formed by passing two stitches 132*a*, 132*b* of suture in orthogonal directions over intersections 118, passing through the tubular seal 130. In some cases, preformed apertures 131 for cross stitch 132 can be formed in the tubular seal 130. In some cases, a portion of the tubular seal 130 sutured by cross stitch 132 includes an internal fabric, such as those discussed below. Each cross stitch 132 can be knotted independently. As shown in FIG. 5C, cross stitches 132 each include a separate knot 137. Additionally, cross stitches 132 can be arranged to not pass through leaflets 200. Cross stitches 132 can be repeated at a plurality of intersections 118 (FIG. 5A) circumferentially around an inflow end of a prosthetic heart valve provided herein such that an entire circumference of tubular seal 130 is securely attached. In some cases, each intersection 118 immediately adjacent to inflow crowns 115 is sutured to tubular seal 130 via a cross stitch provided herein.

Tubular seal 130 can have any suitable structure. In some cases, tubular seal 130 can include an elastic material. In some cases, tubular seal 130 can include one or more layers of an elastomeric polymer. In some cases, tubular seal 130 can include polycarbonate, polyurethane, silicone, polytetrafluoroethylene (PTFE), or a combination thereof. In some cases, tubular seal 130 can include an aliphatic polycarbonate-based thermoplastic urethane. In some cases, tubular seal 130 can include an elastomeric polymer having harnesses ranging from 75 Shore A to 75 Shore D using ASTM standard D2240 in force on Jan. 1, 2014. In some cases, tubular seal 130 can include a polymeric material having the mechanical properties shown in Table I below. Notably, all of the listed ASTM standards refers to the standard in force on Jan. 1, 2014.

TABLE I

| | | ASTM Standard |
|---|---|---|
| Durometer Range Available | 75 Shore A-75 Shore D | D2240 |
| Specific Gravity | 1.10-1.14 | D792 |
| Melt Flow | 2-26 g/10 min (205° C./3.26 kg) | D1238 |

| MECHANICAL PROPERTY RANGES | | | | ASTM Standard |
|---|---|---|---|---|
| Durometer | 75A-B20 | 55D | 75D | 75D |
| Ultimate Tensile Strength (psi) | 400-9000 | 5000-10000 | 3000-8000 | D638 |
| Tensile (psi) | | | | |
| @50% elongation | 350-650 | 1500-1800 | 3000-8000 | D638 |
| @100% elongation | 550-850 | 1800-2200 | 3000-8000 | D638 |
| @200% elongation | 600-1200 | 2800-4200 | | D638 |
| @300% elongation | 1200-2000 | 4200-10000 | | D630 |
| Ultimate Elongation (%) | 350-750 | 200-400 | 100-300 | D638 |

In some cases, tubular seal 130 can include attachment structures to improve the attachment of the tubular seal 130 to leaflets 200 and/or expandable member 110.

Figure 7B:
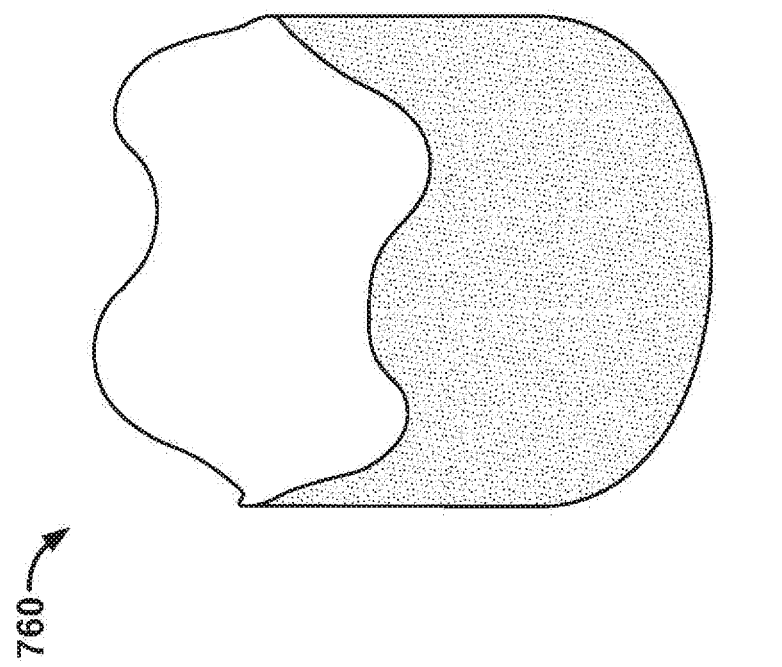
FIGS. 7A and 7B depict exemplary tubular seals having a fabric positioned within a matrix, which can be used in a prosthetic heart valve provided herein.
Figure 7A:
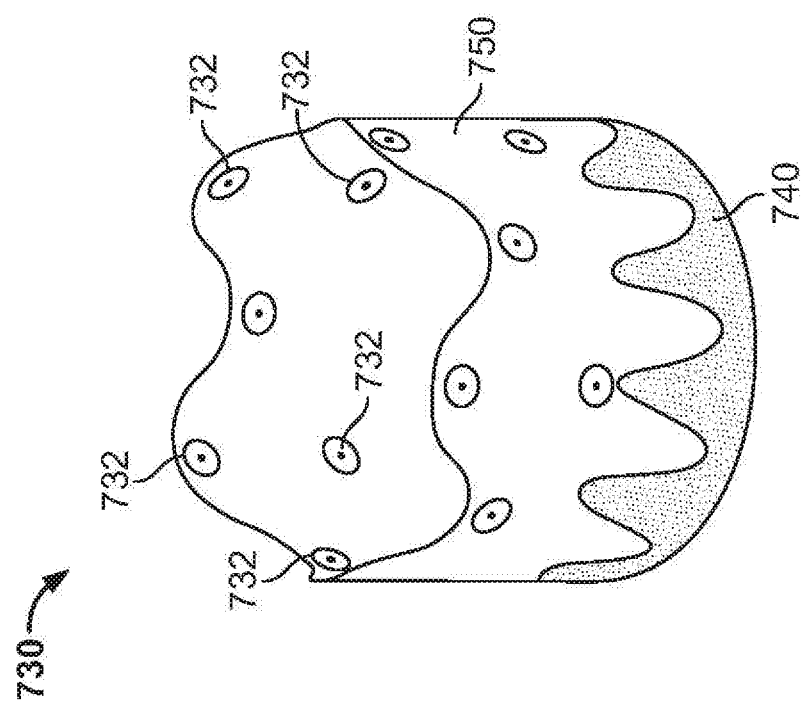

In some cases, such as shown in FIG. 7A a tubular seal 730 can include an inflow end section 740 an outflow end section 750 wherein the inflow end section 740 includes a fabric embedded within elastomeric material and outflow end section 750 includes a plurality of grommets 732. The fabric in inflow end section 740 can be a woven material. In some cases, the fabric can have warp threads and weft threads. In some cases, the fabric can include non-elastomeric fibers. For example, in some cases, the fabric can include polyester fibers, e.g., PES 38/31 manufactured by SaatiTech. In some cases, the fabric is composed of fibers having a thread diameter of about 0.0011 inches (about 27 microns). Because the fabric includes non-elastic fibers, inflow end section 740 and outflow end section 750 have different overall elastic properties. In some cases, tubular seal 730 can be used as tubular seal 130 of prosthetic heart valve 100. In some cases, tubular seal 730 can be used in other prosthetic heart valves provided herein.

As shown in FIG. 7A, an interface between the inflow end section 740 and the outflow end section 750 is non-linear due to a non-linear edge of fabric within the inflow end section 740. As shown, the non-linear edge can be sinusoidal. In some cases, not shown, the non-linear edge can be scalloped. In some cases, the non-linear edge can be zig-zagged, sinusoidal, stepped, scalloped or pointed. Because of the presence of a fabric within inflow end section 740, inflow end section 740 can be thicker than outflow end section 750. For example, in some cases, an inflow end section 740 can have a thickness of about 0.003 inches (about 70 microns) and the outflow end section 750 can have a thickness of about 0.002 inches (about 50 microns). Other dimensions are also suitable. A non-linear edge providing an non-linear interface between the inflow end section 740 and the outflow end section 750 can result an overall diameter increase of a prosthetic heart valve provided herein that tapers more gradually than would be provided by an inflow end section 740 having a linear interface with the outflow end section 750. The non-linear edge of the fabric can also transition the change in elastic properties between outflow end section 750 to inflow end section 740 to mitigate the formation of stress concentrators along the interface with can result in tears of the tubular member. Additionally, the shape of non-linear interface can limit the propagation of tears.

In some cases, the fabric can be arranged in inflow end section 740 to allow for the fabric within inflow end section 740 to be stretched in axial and radial directions. For example, in the case of a woven fabric, the fabric can be arranged to have the warp and the waft extend in directions orthogonal to the axis of the tubular seal to allow for the fabric to flex in both radial and axial directions. In some cases, both the warp and the waft can extend at an angle of between 30 degrees and 60 degrees with the axis of the tubular seal. In some cases, both the warp and the waft can extend at an angle of between 5 degrees and 70 degrees with the axis of the tubular seal. For example, the warp and waft can be arranged within the tubular member 730 to form an angle of about 45 degrees with the axis of the tubular seal. In some cases, the fabric can be a knit fabric arranged to allow for a predetermined amount of stretch in the axial and radial directions.

Additional exemplary tubular seals including a fabric and grommets are described in US Patent Application No. 2013/0090729, which is hereby incorporated by reference in its entirety. In some cases, tubular seals described in US Patent Application No. 2013/0090729 can be modified to include a fabric arranged to allow for it to stretch in a radial direction.

Tubular seal 730 can be created by producing one or more layers of elastomeric polymer, applying the fabric and grommets 732 to the one or more layers of elastomeric polymer, and overcoating the fabric and grommets 732 with one or more additional layers of elastomeric material. In some cases, different layers can have different elastomeric properties. In some cases, tubular seals (e.g., 130, 730, or 760) can include a radially innermost layer including a polycarbonate and a polyurethane; a radially outermost layer including a polycarbonate and a polyurethane; and at least one inner layer disposed between the radially outermost layer and the radially innermost layer including a polycarbonate and a polyurethane. In some cases, the modulus of elasticity of the inner layer is less than the modulus of elasticity of the radially innermost outer layer and the modulus of elasticity of the radially outermost outer layer. In some cases, the elongation to break of the inner layer is greater than the elongation to break of the radially innermost outer layer and the elongation to break of the radially outermost outer layer. Although the radially innermost outer layer and the radially outermost outer layer have been depicted as comprising the same material, it will be appreciated that they may be compositionally the same or different.

Figure 6:
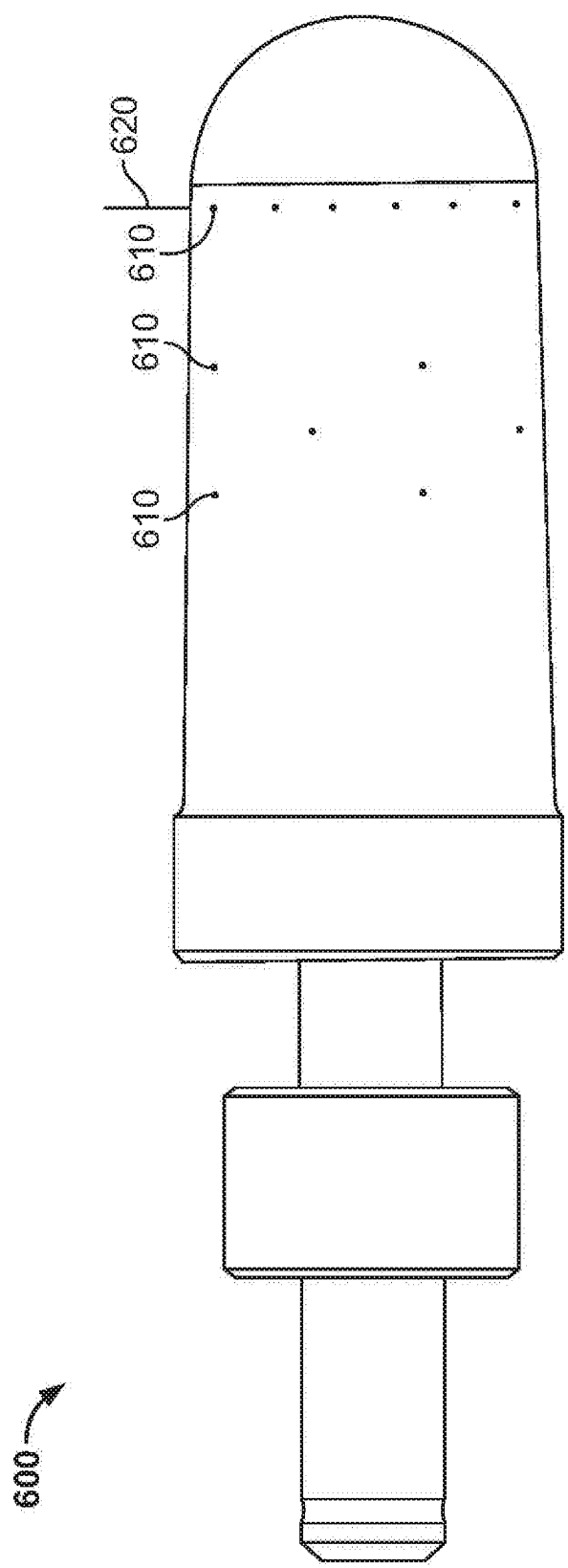
FIG. 6 depicts an apparatus that can be used to form a tubular seal provided herein.

The multilayer tubular seals provided herein (e.g., 130, 730, 760) may be formed in a variety of ways. For example, multilayer tubular seals provided herein may be formed by successive applications of a polymer solution to an appropriately shaped mandrel, such as that illustrated in FIG. 6. Following a careful cleaning of the mandrel 600, the mandrel may be mounted to an appropriate holding fixture in a spray booth. A first coating composition comprising a carrier and at least one polymer may be applied to the mandrel 600 and subsequently dried to form a first coated mandrel. In some cases, the first coating composition comprises a polycarbonate, a polyurethane, and a volatile carrier. The coating composition may be applied as a single layer or multiple layers to achieve the desired dried coating thickness. The grommets 732 and the fabric may be positioned on the first coated mandrel, for example by inserting locating pins 620 in apertures 610 in the tapered mandrel 600 which align with corresponding perforations 30 provided in the grommets 32, 34, 36 and fabric 40. In FIG. 6, only one pin 620 has been illustrated for clarity. In some instances, it may be desirable to secure the plurality of grommets 732 and the fabric to the mandrel or to an underlying coating layer by applying a drop of a first coating composition, or other adhesive composition, to each item to ensure that it remains properly positioned during subsequent processing. The fabric can be cut to a suitable shape having a non-linear edge using any suitable method. In some cases, the fabric can be die cut. In some cases, the fabric can be cut using a femtosecond laser. In some cases, a femtosecond laser cut fabric mitigate the chances of forming stress concentrators along the edge of the fabric.

A second coating composition comprising a carrier and at least one polymer may be applied to the first coated mandrel, the fabric, and the plurality of grommets. In some cases, the second coating composition comprises a polycarbonate, a polyurethane, and a volatile carrier. The carrier of the second coating composition may be removed, thereby forming a second coated mandrel. The second coating composition may be applied as a single layer or as multiple layers to achieve the desired dried coating thickness. In some cases, the second coating composition may be different from the first coating composition. In some cases, the second coating composition may be the same as the first coating composition.

In some cases, a third coating composition comprising a carrier and at least one polymer may be applied to the second coated mandrel. In some cases, the third coating composition comprises a polycarbonate, a polyurethane, and a volatile carrier. The carrier of the third coating composition may be removed thereby forming a tubular seal precursor. The third coating composition may be applied as a single layer or multiple layers to achieve the desired dried coating thickness. In some cases, the third coating composition may be different from the first coating composition. In some cases, the third coating composition may be the same as the first coating composition. In some cases, the third coating composition may be different from the second coating composition. In some cases, the third coating composition may be the same as the second coating composition. Following removal of the carrier from the third coating composition, the tubular seal precursor may be inspected to ensure that it is fully formed and meets dimensional specifications, such as a thickness specification. For example, a suitable thickness for the tubular seal precursor can range from about 0.001 inches to about 0.0030 inches (about 30 microns to about 75 microns) or from about 0.002 inches to about 0.0047 inches (about 50 microns to about 120 microns). Other suitable thicknesses for the tubular seal precursor include a range from about 0.0008 inches to about 0.002 inches (about 20 microns to about 40 microns), about 0.001 inches to about 0.002 inches (about 30 microns to about 50 microns), about 0.002 inches to about 0.0029 inches (about 50 microns to about 75 microns), about 0.002 inches to about 0.004 inches (about 50 microns to about 100 microns), about 0.004 inches to about 0.0047 inches (about 100 microns to about 120 microns), about 0.004 inches to about 0.0059 inches (about 100 microns to about 150 microns), about 0.0059 inches to about 0.0079 inches (about 150 microns to about 200 microns), as well as any thickness value within any of the listed ranges. Also, the tubular seal precursor may be inspected to ensure that it meets certain functional specifications, e.g., tensile and frictional specifications. The tubular seal precursor may then be trimmed, for example by laser cutting or blade cutting, to conform to dimensional specifications; and removed from the tapered seal-forming mandrel thereby forming a tubular seal. In some cases, at least some preformed apertures for suturing tubular seal to expandable member 110 and/or leaflets 200 can be performed by laser cutting. In some cases, at least some of the grommets may be formed by a laser cutting operation performed on a tubular seal precursor. For example, grommets 732 may be added to the multilayer, generally cylindrical seal, in a step not illustrated, as a proximal band. Subsequent laser cutting of the tubular seal precursor would then simultaneously form grommets 732 by removing the portions of the proximal band located between the projections.

In some cases, coating compositions may be selected to provide a relatively stiff dried polymer such as a dried polymer having a Shore D hardness of about 55. In some cases, coating compositions may be selected to provide a relatively elastomeric dried polymer such as a dried polymer having a Shore A hardness of about 80. For example, the first and third dried polymer layers may have a Shore D hardness of 55 and the second layer may have a Shore A hardness of 80.

Although in the example above three polymer layers were employed, it will be appreciated that a greater or lesser number of layers may be employed and that each of the three or more layers may comprise two or more sublayers. Additionally, although the plurality of grommets and the fabric were positioned between the first and second coating layers in the example, they could have been positioned elsewhere within the tubular seal including within a layer, or on the radially innermost or radially outermost surface of the tubular seal.

The mandrel 600 of FIG. 6 includes a taper which results in a tubular seal having a slightly smaller diameter proximal end compared to the diameter of the distal end. The taper allows the tubular seal to be removed from the mandrel with relative ease upon completion of the fabrication process. The smaller proximal diameter of the tubular seal tends to cause the proximal projections to lie more firmly against the anchor element of the replacement heart valve. In some cases, the surface of the mandrel may be textured, for example by bead blasting, to create a tubular seal having a lower apparent contact area. In combination with the selection of a relatively hard outer layer, a textured seal surface is believed to result in a lower friction surface.

In some cases, as shown in FIG. 7B, a tubular seal 760 can include a woven or non-woven fabric embedded throughout a polymer or metal matrix structure. In some cases, the matrix structure can be made of elastomeric material. In some cases, tubular seal 760 can be made of the fabric alone. The fabric can include non-elastic fibers but be arranged to allow for the tubular seal to stretch in axial and radial directions. In some cases, the fabric can be a knit fabric arranged to allow for a predetermined amount of stretch in the axial and radial directions. In some cases, the fabric can be made of a polymer, for example, a polyester. In some cases, the fabric can have a thickness ranging from about 0.002 inches to about 0.003 inches (about 40 to about 80 microns). In some cases, the fabric can be woven such that spacings between individual fibers create openings in the fabric that together constitutes about 20% to about 40% of a fabric surface.

A number of embodiments of the invention have been described. Nevertheless, it will be understood that various modifications may be made without departing from the spirit and scope of the invention. Accordingly, other embodiments are within the scope of the following claims.

What is claimed is:

1. A prosthetic heart valve comprising at least two leaflets being secured together along aligned edges thereof by a stitch of a single thread, the stitch comprising at least one loop extending through a first aperture, around the aligned edges, and back through the first apertures;
   wherein each leaflet has a body portion and two opposite sleeve portions, the body portion being defined by a bottom edge and two side edges adjacent each sleeve portion, wherein each of the at least two leaflets are aligned and stitched along a first side edge.

2. The prosthetic heart valve of claim 1, wherein the stitch further comprises at least one segment of thread extending from the first aperture to a second aperture in a direction parallel to the aligned edges of the at least two leaflets.

3. The prosthetic heart valve of claim 2, wherein the stitch comprises a second loop extended through the second aperture, around the aligned edges, and back through the second aperture.

4. The prosthetic heart valve of one of claim 1, wherein the stitch comprises at least three loops each extending from an aperture, around the aligned edges, and back to that aperture.

5. The prosthetic heart valve of claim 4, wherein the stitch runs in a forward direction having thread pass through a set of apertures and back in a reverse direction having the thread again pass through the set of apertures.

6. The prosthetic heart valve of claim 5, wherein each aperture has two loops extending from that aperture, around the aligned edges, and tack to that aperture, wherein one loop is from the stitch running in the forward direction and one loop is from the stitch running in the reverse direction.

7. The prosthetic heart valve of claim 5, wherein segments of thread extending between adjacent apertures in the forward direction are on an opposite side of the two leaflets from the segments of thread extending between adjacent apertures in the reverse direction.

8. The prosthetic heart valve of claim 1, wherein the leaflets define notches between the two side edges and the adjacent sleeve portion.

9. The prosthetic heart valve of claim 1, wherein the stitch runs along a side edge from a bottom edge to a notch.

10. The prosthetic heart valve of claim 1, further comprising a plurality of support element each supporting sleeve portions each leaflet along a line approximately aligned the stitch.

11. A prosthetic heart valve comprising:
    at least three leaflets secured together along side edges thereof by a stitch of a single thread;
    a tubular expandable member secured to an out flow end of the at least three leaflets; and
    a tubular seal secured to an inflow end bottom edge of the at least three leaflets and to an outer surface of the tubular expandable member;
    wherein the stitch is formed using between 3 and 20 apertures and includes between 3 and 40 loops each extending from an aperture, around the aligned side edges, and back to that aperture.

12. The prosthetic heart valve of claim 11, wherein the tubular expandable member is a braided stent and wherein tubular seal is secured to the braided stent by a plurality of cross stitches connecting the tubular seal to a pair of overlapping wire members of the braided stent.

13. The prosthetic heart valve of claim 11, wherein the tubular seal comprises a woven fabric and the at least three leaflets are secured to the tubular seal in a portion of the tubular seal comprising the woven fabric.

14. The prosthetic heart valve of claim 13, wherein the woven fabric can have a thickness range from about 40 to about 80 microns.

15. The prosthetic heart valve of claim 13, wherein the woven fabric is disposed within a polymer matrix.

16. The prosthetic heart valve of claim 11, wherein the at least one leaflet comprises bovine or porcine pericardium tissue or a synthetic material.

17. The prosthetic heart valve of claim 11, wherein one or more stitches can be repeated at a plurality of intersections circumferentially around the inflow end bottom edge.

18. A prosthetic heart valve comprising:
    at least three leaflets secured together along side edges thereof by a stitch of a single thread, at least one leaflet being secured to at least a second leaflet by a running stitch, the running stitch being a square stitch;
    a tubular expandable member secured to an out flow end of the at least three leaflets; and
    a tubular seal secured to an inflow end bottom edge of the at least three leaflets and to an outer surface of the tubular expandable member.

* * * * *